(12) United States Patent
Wallach et al.

(10) Patent No.: US 7,455,977 B2
(45) Date of Patent: Nov. 25, 2008

(54) METHODS OF DETERMINING THE LEVEL OF HUMAN TBP-II WITH ANTI-TBP-II ANTIBODY

(75) Inventors: David Wallach, Rehovot (IL); Jacek Bigda, Gdansk (PL); Igor Beletsky, Pushino (RU); Igor Mett, Rehovot (IL); Hartmut Engelmann, Munich (DE)

(73) Assignee: Yeda Research and Development Co. Ltd., Rehovot (IL)

( * ) Notice: Subject to any disclaimer, the term of this patent is extended or adjusted under 35 U.S.C. 154(b) by 752 days.

(21) Appl. No.: 10/632,929

(22) Filed: Aug. 4, 2003

(65) Prior Publication Data

US 2004/0161858 A1 Aug. 19, 2004

Related U.S. Application Data

(60) Division of application No. 09/800,908, filed on Mar. 8, 2001, now Pat. No. 6,602,993, which is a division of application No. 08/477,347, filed on Jun. 7, 1995, now Pat. No. 6,232,446, which is a continuation-in-part of application No. 07/930,443, filed on Aug. 19, 1992, which is a continuation of application No. 07/524,263, filed on May 16, 1990, now abandoned, said application No. 08/477,347 is a continuation-in-part of application No. 08/450,972, filed on May 25, 1995, now abandoned, which is a continuation of application No. 08/115,685, filed on Sep. 3, 1993, now abandoned.

(30) Foreign Application Priority Data

| May 18, 1989 | (IL) | 90339 |
| Aug. 6, 1989 | (IL) | 91229 |
| Apr. 6, 1990 | (IL) | 94039 |
| Sep. 3, 1992 | (IL) | 103051 |
| Jul. 8, 1993 | (IL) | 106271 |

(51) Int. Cl.
*G01N 33/53* (2006.01)

(52) U.S. Cl. ..................... 435/7.1

(58) Field of Classification Search ............ None
See application file for complete search history.

(56) References Cited

U.S. PATENT DOCUMENTS

| 4,677,063 A | 6/1987 | Mark et al. |
| 4,898,818 A | 2/1990 | Nakai et al. |
| 4,948,875 A | 8/1990 | Tanaka et al. |
| 4,990,455 A | 2/1991 | Yamagishi et al. |
| 5,344,915 A | 9/1994 | LeMaire et al. |
| 5,610,279 A * | 3/1997 | Brockhaus et al. ....... 530/387.3 |
| 5,700,466 A * | 12/1997 | Wolpe et al. ............. 424/145.1 |
| 6,232,446 B1 | 5/2001 | Wallach et al. |

FOREIGN PATENT DOCUMENTS

EP  0334165 A2 * 9/1989

OTHER PUBLICATIONS

Shalaby et al., J. Exp. Med. 172: 1517-1520, 1990.*
Engelmann, H., et al., "Antibodies to a Soluble Form of a Tumor Necrosis Factor (TNF) Receptor Have TNF-like Activity", Journal of Biological Chemistry, 265:14497-1504 (1990).
Espevik, T., et al., "Characterization of Binding and Biological Effects of Monoclonal Antibodies Against a Human Tumor Necrosis Factor Receptor", J. Exp. Med., 171:415-426 (1990).
Banner et al, "Crystal Structure of the Soluble Human 55 kd TNF Receptor-human TNF Beta Complex: Implications for TNF Receptor Activation", *Cell* 73(3):431-451 (1993).
Jaattela M, "Biologic Activities and Mechanisms of Action of Tumor Necrosis Factor-alpha/cachectin", *Lab Invest* 64(6):724-742 (1991).
Marsters et al, "Identification of Cystein-rich Domains of the Type 1 Tumor Necrosis Factor Receptor Involved in Ligand Binding", *J Biol Chem* 267(9):5747-5750 (1992).
Rothe et al, "Tumor Necrosis Factor Receptors-structure and Function", *Immunol Res* 11(2):81-90 (1992).

* cited by examiner

*Primary Examiner*—Phillip Gambel
(74) *Attorney, Agent, or Firm*—Browdy and Neimark, P.L.L.C.

(57) ABSTRACT

Antibodies to tumor necrosis factor receptors (TNF-Rs) are disclosed together with methods of producing them and methods of use of such antibodies in immunoassays and purification of TBP-II by affinity chromatography. A diagnostic assay for endogenous antibodies to TBP-II is also disclosed.

2 Claims, 17 Drawing Sheets

FIG. 2
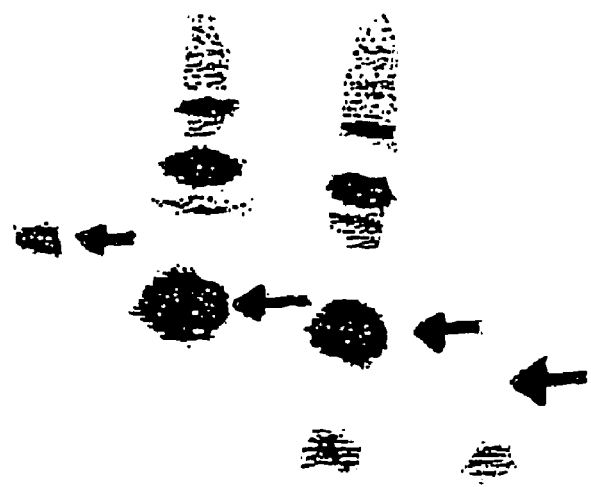
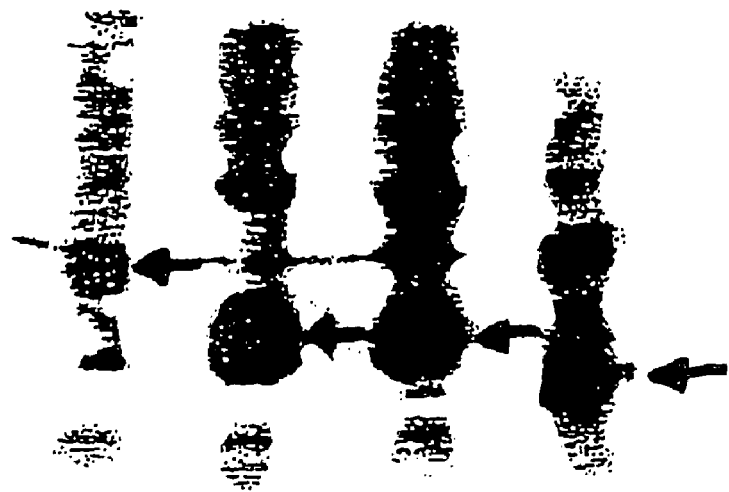

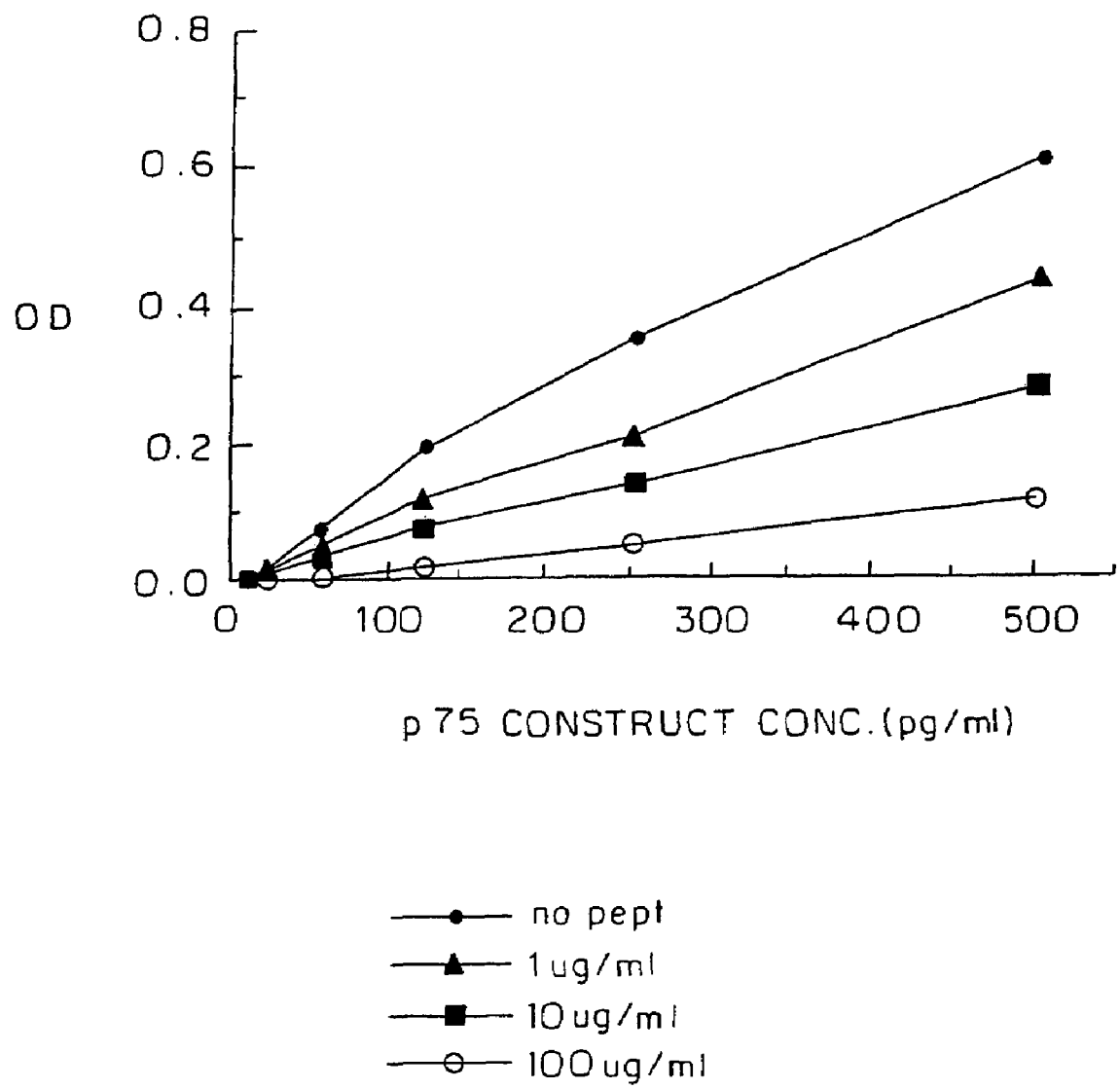

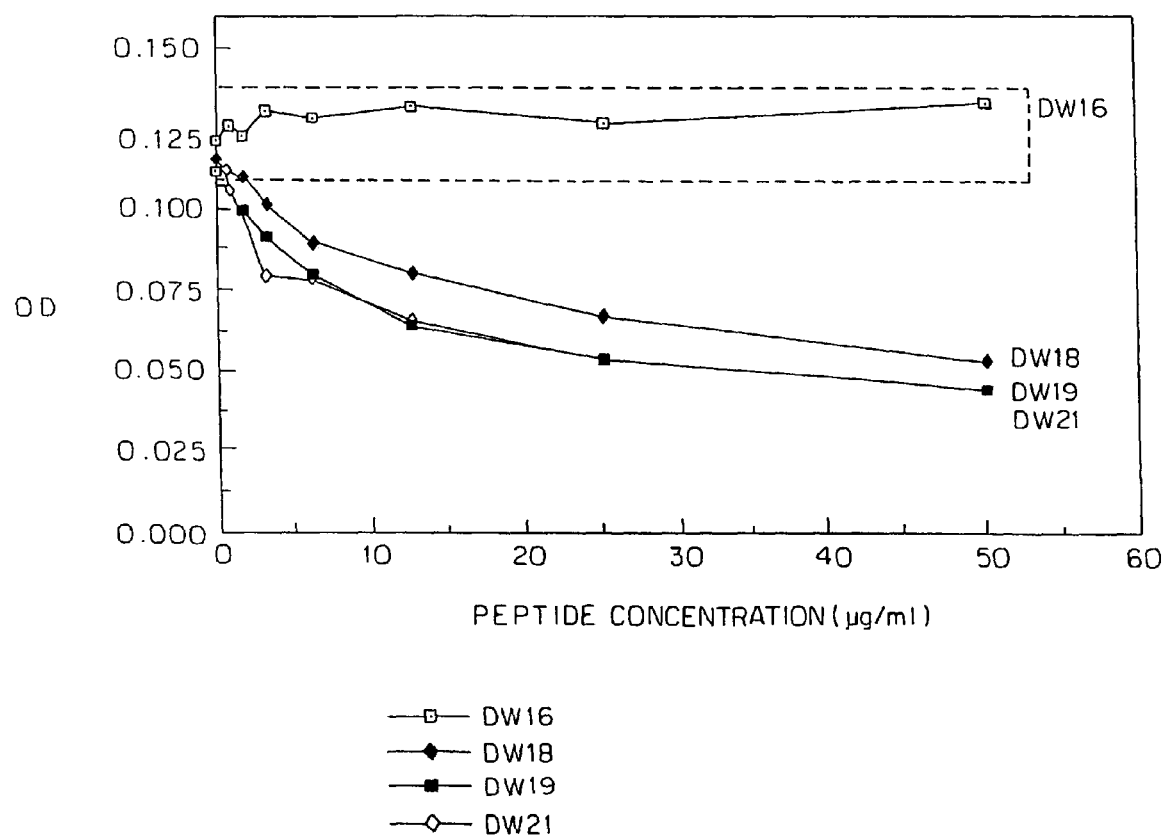

FIG. 5A

```
1
gcgagcgcag cggagcctgg agagaaggcg ctgggctgcg agggcgcgag ggcgcgaggg caggggggcaa ccggaccccg
81
cccgcaccc atg gcg ccc gtc gcc gtc tgg gcc gcg ctg gcc gtc gga ctg gag ctc tgg gct gcg
           Met Ala Pro Val Ala Val Trp Ala Ala Leu Ala Val Gly Leu Glu Leu Trp Ala Ala
147                -22
gcg cac gcc ttg ccc gcc cag ┌gtg gca ttt aca ccc tac gcc ccg gag ccc ggg agc aca tgc cgg
Ala His Ala Leu Pro Ala Gln │Val Ala Phe Thr Pro Tyr Ala Pro Glu Pro Gly Ser Thr Cys Arg
213             -1 +1       │                                                  10
ctc aga gaa tac tat gac cag  aca gct cag atg tgc tgc agc aaa tgc tcg ccg ggc caa cat gca
Leu Arg Glu Tyr Tyr Asp Gln  Thr Ala Gln Met Cys Cys Ser Lys Cys Ser Pro Gly Gln His Ala
279 . . . . . . . . . . . .  . . . . . . . . . 32 . . . . . . . . . . . . . . . . . . .
aaa gtc ttc tgt acc aag acc  tcg gac acg gtg tgt gac tcc tgt gag gac agc aca tac acc cag
Lys Val Phe Cys Thr Lys Thr  Ser Asp Thr Val Cys Asp Ser Cys Glu Asp Ser Thr Tyr Thr Gln
345 . . . . . . . . . . . .  . . . . . . . . . 54 . . . . . . . . . . . . . . . . . . .
ctc tgg aac tgg gtt ccc gag  tgc ttg agc tgt ggc tcc cgc tgt agc tct gac cag gtg gaa act
Leu Trp Asn Trp Val Pro Glu  Cys Leu Ser Cys Gly Ser Arg Cys Ser Ser Asp Gln Val Glu Thr
411 . . . . . . . . . . . .  . . . . . . . . . 76 . . . . . . . . . . . . . . . . . . .
caa gcc tgc act cgg gaa cag  aac cgc atc tgc acc tgc agg ccc ggc tgg tac tgc gcg ctg agc
Gln Ala Cys Thr Arg Glu Gln  Asn Arg Ile Cys Thr Cys Arg Pro Gly Trp Tyr Cys Ala Leu Ser
477 . . . . . . . . . . . .  . . . . . . . . . 98 . . . . . . . . . . . . . . . . . . .          │
aag cag gag ggg tgc cgg ctg  tgc gcg ccg ctg cgc aag tgc cgc ccg ggc ttc ggc gtg gcc aga       │ TBPII
Lys Gln Glu Gly Cys Arg Leu  Cys Ala Pro Leu Arg Lys Cys Arg Pro Gly Phe Gly Val Ala Arg       │
543 . . . . . . . . . . . .  . . . . . . . . .120 . . . . . . . . . . . . . . . . . . .
cca gga act gaa aca tca gac  gtg gtg tgc aag ccc tgt gcc ccg ggg acg ttc ttc aac acg act
Pro Gly Thr Glu Thr Ser Asp  Val Val Cys Lys Pro Cys Ala Pro Gly Thr Phe Ser Asn Thr Thr
609 . . . . . . . . . . . .  . . . . . . . . .142 . . . . . . . . . . . . . . . . . . .
tca tcc acg gat att tgc agg  ccc cac cag atc tgt aac gtg gtg gcc atc ccg ggg aat gca agc
Ser Ser Thr Asp Ile Cys Arg  Pro His Gln Ile Cys Asn Val Val Ala Ile Pro Gly Asn Ala Ser
675 . . . . . . . . . . . .  . . . . . . . . .164 . . . . . . . . . . . . . . . . . . .
atg gat gca gtc tgc acg tcc acg tcc ccc acc cgg agt atg gcc cca ggg gca gta┘cac tta ccc
Met Asp Ala Val Cys Thr Ser Thr Ser Pro Thr Arg Ser Met Ala Pro Gly Ala Val His Leu Pro
741 . . . . . . . . . . . . . . . . . . . . . 186 . . . . . . . . . . . . . . . . . . .
```

FIG.5B

```
cag cca gtg tcc aca cga tcc caa cac acg cag cca act cca gaa ccc agc act gct cca agc acc
Gln Pro Val Ser Thr Arg Ser Gln His Thr Gln Pro Thr Pro Glu Pro Ser Thr Ala Pro Ser Thr
807                                                    208
tcc ttc ctg ctc cca atg ggc ccc agc ccc cca gct gaa ggg agc act ggc gac ttc gct ctt cca
Ser Phe Leu Leu Pro Met Gly Pro Ser Pro Pro Ala Glu Gly Ser Thr Gly Asp Phe Ala Leu Pro    TRANSMEMBRANE
873                                                    230
gtt gga ctg att gtg ggt gtg aca gcc ttg ggt cta cta ata ata gga gtg gtg aac tgt gtc atc
Val Gly Leu Ile Val Gly Val Thr Ala Leu Gly Leu Leu Ile Ile Gly Val Val Asn Cys Val Ile    DOMAIN
939                                           252
atg acc cag gtg aaa aag aag ccc ttg tgc ctg cag aga gaa gcc aag gtg cct cac ttg cct gcc
Met Thr Gln Val Lys Lys Lys Pro Leu Cys Leu Gln Arg Glu Ala Lys Val Pro His Leu Pro Ala
1005                                                  274
gat aag gcc cgg ggt aca cag ggc ccc gag cag cag cac ctg ctg atc aca gcg ccg agc tcc agc
Asp Lys Ala Arg Gly Thr Gln Gly Pro Glu Gln Gln His Leu Leu Il- Thr Ala Pro Ser Ser Ser
1071                                                  296
agc agc tcc ctg gag agc tcg gcc agt gcg ttg gac aga agg gcg ccc act cgg aac cag cca cag
Ser Ser Ser Leu Glu Ser Ser Ala Ser Ala Leu Asp Arg Arg Ala Pro Thr Arg Asn Gln Pro Gln
1137                                                  318
gca cca ggc gtg gag gcc agt ggg gcc gcg gag gcc cgg gcc agc acc ggg agc tca gat tct tcc
Gly Ala Gly Glu Ala Arg Ala Ser Thr Gly Ser Ser Asp Ser Ser Pro Gly Gly His Gly Thr Gln
1203                                                  340
ctt ggt ggc cat ggg acc cag gtc aat gtc acc tgc atc gtg aac gtc tgt agc agc tct gac cac
Ala Pro Gly Val Glu Ala Ser Val Asn Val Thr Cys Ile Val Asn Val Cys Ser Ser Ser Asp His
1269                                                  362
agc tca cag tgc tcc tcc caa gcc agc tcc aca atg gga gac aca gat tcc agc ccc tcg gag tcc
Ser Ser Gln Cys Ser Ser Gln Ala Ser Ser Thr Met Gly Asp Thr Asp Ser Ser Pro Ser Glu Ser
1335                                                  384
ccg aag gac gag cag gtc ccc ttc tcc aag gag gaa tgt gcc ttt cgg tca cag ctg gag acg cca
Pro Lys Asp Glu Gln Val Pro Phe Ser Lys Glu Glu Cys Ala Phe Arg Ser Gln Leu Glu Thr Pro
1401                                                  406
gag acc ctg ctg ggg agc acc gaa gag aag ccc ctg ccc ctt gga gtg cct gat gct ggg atg aag
Glu Thr Leu Leu Gly Ser Thr Glu Glu Lys Pro Leu Pro Leu Gly Val Pro Asp Ala Gly Met Lys
1467                                                  428
ccc agt taa ccaggccggt gtgggctgtg tcgtagccaa ggtgggctga gccctggcag gatgaccctg cgaagggc
Pro Ser End
    439
```

FIG. 5C

```
1545
cctggtcctt ccaggccccc accactagga ctctgaggct ctttctgggc caagttcctc tagtgccctc cacagccgca
gcctccctct gacctgcagg ccaagagcag aggcagcgag ttggggaaag cctctgctgc catggtgtgt ccctctcgga
aggctggctg ggcatggacg ttcggggcat gctgggcaa gtccctgact ctctgtgacc tgccccgccc agctgcacct
gccagcctgg cttctggagc ccttgggttt tttgtttgtt tgtttgtttg tttgtttgtt tctcccctg ggctctgccc
agctctggct tccagaaaac cccagcatcc ttttctgcag aggggctttc tggagaggag ggatgctgcc tgagtcaccc
atgaagacag gacagtgctt ctgcctgagg cagagactgc gggatggtcc tggggctctg tgtagggagg aggtggcagc
cctgtaggga acggggtcct tcaagttagc tcaggaggct tggaaagcat cacctcaggc caggtgcagt ggctcacgcc
tatgatccca gcactttggg aggctgaggc gggtggatca cctgaggtta ggagttcgag accagcctgg ccaacatggt
aaaaccccat ctctactaaa aatacagaaa ttagccgggc ......3683
                                                   acctcaggc caggtgcagt ggctcacgcc
                                             2075
```

FIG.11A

```
      1/1                                                31/11
#70   GTG AAA CTG CAG GAG TCT GGA CCT GAG CTG GTG AAG CCT GGG GCC TCA GTG AAG ATT TCC
      V   K   L   Q   E   S   G   P   E   L   V   K   P   G   A   S   V   K   I   S
      1/1                                                31/11
#32                                   CCT GAG CTG GTG GCT CCT GGG GCC TCA GTG AAG ATT TCC
                                      P   E   L   V   A   P   G   A   S   V   K   I   S
      1/1                                                31/11
#57   GTG TCC CTG CAG GAG TCT GGG GGA GGC TTA GTG CAG CCT GGA GGG TCC CGG AAA CTC TCC
      V   S   L   Q   E   S   G   G   G   L   V   Q   P   G   G   S   R   K   L   S

61/21                                              91/31
#70   TGC AAA ACT TCT GGC TTC GCA TTC AGT CAT TCT TGG ATG AAC TGG GTG AGG CAG AGG CCT
      C   K   T   S   G   F   A   F   S   H   S   W   M   N   W   V   R   Q   R   P
      61/21                                              91/31
#32   TGC AAA GCT TCT GGC TAC GCA TTC AGT CAC TCT TGG ATG AAC TGG GTG AAG CAG AGG CCT
      C   K   A   S   G   Y   A   F   S   H   S   W   M   N   W   V   K   Q   R   P
      61/21                                              91/31
#57   TGT GCA GCT TCT GGA TTC ACT TTC AGT AGC TTT GGA ATG CAC TGG GTT CGT CAG GCT CCA
      C   A   A   S   G   F   T   F   S   S   F   G   M   H   W   V   R   Q   A   P

121/41                                             151/51
#70   GGA CAG GGT CTT GAA TGG ATT GGA CGG ATT TAT CCT GGA GAT GGA AAT ACT GAT TAC CCT
      G   Q   G   L   E   W   I   G   R   I   Y   P   G   D   G   N   T   D   Y   N
      121/41                                             151/51
#32   GGA AAG GGT CTT GAG TGG ATT GGA CGG ATT CAT CCT GGA GAT GGA GAC ACT GAC TAC AAT
      G   K   G   L   E   W   I   G   R   I   H   P   G   D   G   D   T   D   Y   N
      121/41                                             151/51
#57   GAG AAG GGG CTG GAG TGG GTC GCA TAC ATT AGT AGT GGC AGT AGT ACC CTC CAC TAT GCA
      E   K   G   L   E   W   V   A   Y   I   S   S   G   S   S   T   L   H   Y   A
```

FIG.11B

```
     181/61                                          211/71
#70  GGG AAG TTC CAG GGC CAG GCC ACA CTG ACT GCA GAC AAA TCT TCC AGC ACA GCC TAC ATG
      G   K   F   Q   G   Q   A   T   L   T   A   D   K   S   S   S   T   A   Y   M
     181/61                                          211/71
#32  GGG AAC TTC AGG GGC AAG GCC ACA CTG ACT GCA GAC ACA TCC TCC AGC TCA GCC TAC ATG
      G   N   F   R   G   K   A   T   L   T   A   D   T   S   S   S   S   A   Y   M
     181/61                                          211/71
#57  GAC ACA GTG AAG GGC CGA TTC ACC ATC TCC AGA GAC AAT CCC AAG AAC ACG CTG TTC CTG
      D   T   V   K   G   R   F   T   I   S   R   D   N   P   K   N   T   L   F   L
```

```
     241/81                                          271/91
#70  CAA CTC TTC AGT CTG ACC TCT GTG GAC TCT GCA GTC TAT TTT TGT GCA CCC GGC CGT TGG
      Q   L   F   S   L   T   S   V   D   S   A   V   Y   F   C   A   P   G   R   W
     241/81
#32  CAG CTC AGC AGC CTG ACC TCT GTG GAT TCT GCG GTC TAC TTC TGT GCA CCC GGC CGT TGG
      Q   L   S   S   L   T   S   V   D   S   A   V   Y   F   C   A   P   G   R   W
     241/81                                          271/91
#57  CAA ATG AAA CTA CCC TCA CTA TGC TAT GGA CTA CTG GGG CCA AGG GAC CAC GGT CAC CGT
      Q   M   K   L   P   S   L   C   Y   G   L   L   G   P   R   D   H   G   H   R
```

```
     301/101                             331/111
#70  TAC CTC GAA GTC TGG GGC CAA GGG ACC ACG GTC ACC GTC TCC TCA
      Y   L   E   V   W   G   Q   G   T   T   V   T   V   S   S
     301/101
#32  TAC CTC GAG GTC TGG GGC CAA GGG ACC ACG GTC ACC GTC TCC TCA
      Y   L   E   V   W   G   Q   G   T   T   V   T   V   S   S
     301/101
#57  CTC CTC A
      L   L
```

FIG. 12

```
                                31/11
                            TCC TCC CTG GCT ATG TCA GTA GGA CAG ATG GTC ACT
                             S   S   L   A   M   S   V   G   Q   M   V   T
61/21                                    91/31
ATG AGC TGC AAG TCC AGT CAG AGC CTT TTA ACT AGT AGC ACT CAA AAG AAC TCT TTG GCC
 M   S   C   K   S   S   Q   S   L   L   T   S   S   T   Q   K   N   S   L   A
121/41                                   151/51
TGG TAC CAG CAG ACA CCA GGA CAG TCT CCT AAA CTT CTG ATA TAC TTT GCA TCC ACT AGG
 W   Y   Q   Q   T   P   G   Q   S   P   K   L   L   I   Y   F   A   S   T   R
181/61                                   211/71
CTA TCT GGG GTC CCT GAT CGC TTC ATA GGC AGT GGA TCT GGG ACA GAT TTC ACT CTT ACC
 L   S   G   V   P   D   R   F   I   G   S   G   S   G   T   D   F   T   L   T
241/81                                   271/91
ATC AGC AGT GTG CAG GCT GAA GAC CTG GCA GAT TAC TTC TGT CAG CAA CAT TAT AGC ACT
 I   S   S   V   Q   A   E   D   L   A   D   Y   F   C   Q   Q   H   Y   S   T
301/101                                  331/111
CCA TTT ACG TTC GGC TCG GGG ACA AAG TTG GAA ATA GAG CGG GCT GAT GCT GCA CCA ACT
 P   F   T   F   G   S   G   T   K   L   E   I   E   R   A   D   A   A   P   T
361/121
GTA TCC ATC TTC CCA CCA TCC A
 V   S   I   F   P   P   S
```

FIG. 13

```
hu p55 TNF-R (3-42)    VCPQGKYIHPQNN----SICC-TKCHKGTYLYND--CPGPGQDTDCR
hu p75 TNF-R (39-76)   TCRLREYYD-QTA----QMCC-SKCSPGQHAKVF--CTKTS-DTVCD
hu FAS       (31-67)   QNLEGLH-HDGQF------CH-KPCPPGERKARD--CTVNGDEPDCV
hu NGF-R     (3-37)    ACPTGLYTHSGE-------CC-KACNLGEGVAQP--CGA--NQTVCE
hu CDw40     (25-60)   ACREKQYLINSQ-------CC-SLCQPGQKLVSD--CTEF-TETECL
rat Ox40     (25-60)   NCVKDTYPSGHK-------CC-RECQPGHGMVSR--CDHT-RDTVCH hu p55 TNF-R (43-86)   ECESGSFTASEHHL-RHCLSC-SKCRKENGQVEISSCTVD-RDTVCG
hu p75 TNF-R (77-119)  SCEDSTYTQLWNWV-PECLSCGSRCSDD--QVETQACTRE-QNRICT
hu FAS       (68-112)  PCQEGKEYTDKAHFSSKCRRC-RLCDEGHGLEVEINCTRT-QNTKCR
hu NGF-R     (38-80)   PCLDSVTSSDVVSATEPCKPC-TECVGLQSHSAP--CVEA-DDAVCR
hu CDw40     (61-104)  PCGESEFLDTWHRETN-CHQH-KYCDPNLGLRVQQKGTSE-TDTICT
rat Ox40     (61-104)  PC-EPGFYNEAVNY-DTCKQC-TQCNHRSGSELKQNCTPT-EDTVCQ hu p55 TNF-R (87-126)  -CRKNQYRHYWSENLFQCFNC---SLCLHGT-VHLSCQEK-QNTVC-
hu p75 TNF-R (120-162) -CRPGWYCA--LSKQEGCRLCAPLRKCRPGFGVARPGTET-SDVVCK
hu FAS       (113-149) -CKPNFFCN--STVCEHCDPC---TKCEHGI-IKE-CTLT-SNTKC-
hu NGF-R     (81-119)  -CAYGYYQD---ETTGRCEAC---RVCEAGSGLVFSCQDK-QNTVCE
hu CDw40     (105-144) -CEEGWHC-----TSEACESCVLHRSCSPGFGVKQIATGV-SDTICE
rat Ox40     (105-123) -CRPGTQP-----RQDS--------SHKLGVD---------CV hu p55 TNF-R (127-155) TCHAGFFLR--ENE---CVSC-SNCKKSL------ECTK-----LC-
hu p75 TNF-R (163-201) PCAPGTFSNTTSST-DICRPH-QICN----VVA--IPGNASMDAVCT
hu NGF-R     (120-161) ECPDGTYSDEAHHV-DPCLPC-TVCEDTERQLR--ECTRW-ADAECE
hu CDw40     (145-186) PCPVGFFSNVSSAF-EKCHP--TSCETKDLVVQ--QAGTNKTDVCG
rat Ox40     (124-164) PCPPGHFSPGSHQ---ACKPW-TNCTLSGKQIR--HPASNSLDTVCE
```

METHODS OF DETERMINING THE LEVEL OF HUMAN TBP-II WITH ANTI-TBP-II ANTIBODY

CROSS REFERENCE TO RELATED APPLICATIONS

The present application is a division of U.S. application Ser. No. 09/800,908, filed Mar. 8, 2001, now issued as U.S. Pat. No. 6,602,993, which is a division of 08/477,347, filed Jun. 7, 1995, now issued as U.S. Pat. No. 6,232,446, which is a continuation-in-part of U.S. application Ser. No. 07/930,443, filed on Aug. 19, 1992, and U.S. application Ser. No. 08/450,972, filed May 25, 1995, now abandoned. The entire contents of said applications are hereby incorporated herein by reference. Application Ser. No. 07/930,443, filed on Aug. 19, 1992, is a continuation of application no. 07/524,263, filed May 16, 1990, now abandoned. Application Ser. No. 08/450,972, filed May 25, 1995, is a continuation of application no. 08/115,685, filed Sep. 3, 1993, now abandoned.

FIELD OF THE INVENTION

The present invention relates to ligands to Tumor Necrosis Factor receptors (TNF-Rs) which inhibit the effect of TNF but not its binding to the TNF-Rs, as well as to ligands interacting with other receptors of the TNF/NGF family.

BACKGROUND OF THE INVENTION

Tumor necrosis factor (TNF) is a pleiotropic cytokine, produced by a number of cell types, mainly by activated macrophages. It is one of the principal mediators of the immune and inflammatory response. Interest in its function has greatly increased, recently, in view of evidence of the involvement of TNF in the pathogenesis of a wide range of disease states, including endotoxin shock, cerebral malaria and graft-versus-host reaction. Since many of the effects of TNF are deleterious to the organism, it is of great interest to find ways of blocking its action on host cells. An evident target for such intervention are the molecules to which TNF has to bind in order to exert its effects, namely the TNF-Rs. These molecules exist not only in cell-bound, but also in soluble forms, consisting of the cleaved extra-cellular domains of the intact receptors (see Nophar et al., EMBO Journal, 9(10):3269-78, 1990). The soluble receptors maintain the ability to bind TNF, and thus have the ability to block its function by competition with surface receptors.

Another method of TNF inhibition based on the principle of competing with cell-bound molecules, is the use of antibodies recognizing TNF receptors and blocking the ligand binding.

The cell surface TNF-Rs are expressed in almost all cells of the body. The various effects of TNF, the cytotoxic, growth-promoting and others, are all signaled by the TNF receptors upon the binding of TNF to them. Two forms of these receptors, which differ in molecular size: 55 and 75 kilodaltons, have been described, and will be called herein p55 and p75 TNF-R, respectively. It should be noted, however, that there exist publications which refer to these receptors also as p60 and p80.

The TNF-Rs belong to a family of receptors which are involved in other critical biological processes. Examples of these receptors are the low affinity NGF receptor, which plays an important role in the regulation of growth and differentiation of nerve cells. Several other receptors are involved in the regulation of lymphocyte growth, such as CDw40 and some others. Another member of the family is the FAS receptor also called APO, a receptor which is involved in signaling for apoptosis and which, based on a study with mice deficient in its function, seems to play an important role in the etiology of a lupus-like disease. Herein, this family of receptors is called "TNF/NGF receptor family".

One of the most striking features of TNF compared to other cytokines, thought to contribute to the pathogenesis of several diseases, is its ability to elicit cell death. The cell-killing activity of TNF is thought to be induced by the p55 receptor. However, this p55 receptor activity can be assisted by the p75 receptor, through a yet unknown mechanism.

Parent application number 07/524,263 and European Patent publications 398,327 and 412,486 disclose antibodies to the soluble TNF-Rs. These antibodies were found to recognize the soluble TNF-Rs and to inhibit the binding of TNF to the TNF-Rs on the cell surface. Monovalent F(ab) fragments blocked the effect of TNF, while intact antibodies were observed to mimic the cytotoxic effect of TNF.

SUMMARY OF THE INVENTION

The present invention provides a ligand to a member of the TNF/NGF receptor family, which binds to the region or the C-terminal cysteine loop of such a receptor.

Preferably this region includes the amino acid sequence cys-163 to thr-179 in the p75 TNF-R or a corresponding region in another member of the TNF/NGF family.

Preferably, the receptor is the TNF-R, in particular the p75 TNF-R.

One such ligand includes the amino acid sequence for the CDR region of the heavy chain of monoclonal antibody no. 32, shown in FIG. 11 (SEQ ID NO:7), and/or the amino acid sequence for the CDR region of the light chain of this antibody shown in FIG. 12 (SEQ ID NO:11).

Another such ligand includes the amino acid sequence for the CDR region of the heavy chain of monoclonal antibody no. 70 (SEQ ID NO:5) shown in FIG. 11.

Yet another such ligand includes the amino acid sequence for the CDR region of the heavy chain of monoclonal antibody no. 57 (SEQ ID NO:9), shown in FIG. 11.

The above antibodies are called herein, for simplicity's sake, "group 32" antibodies.

In another aspect of the invention, the ligands comprise the scFv of a group 32 antibody.

The ligands may comprise, for example, proteins, peptides, immunoadhesins, antibodies or other organic compounds.

The proteins may comprise, for example, a fusion protein of the ligand with another protein, optionally linked by a peptide linker. Such a fusion protein can increase the retention time of the ligand in the body, and thus may even allow the ligand-protein complex to be employed as a latent agent or as a vaccine.

The term "proteins" includes muteins and fused proteins, their salts, functional derivatives and active fractions The peptides include peptide bond replacements and/or peptide mimetics, i.e., pseudopeptides, as known in the art (see, e.g., Proceedings of the 20th European Peptide Symposium, ed. G. Jung, E. Bayer, pp. 289-336, and references therein), as well as salts and pharmaceutical preparations and/or formulations which render the bioactive peptide(s) particularly suitable for oral, topical, nasal spray, ocular, pulmonary, I.V. or subcutaneous delivery, depending on the particular treatment indicated. Such salts, formulations, amino acid replacements and pseudopeptide structures may be necessary and desirable to enhance the stability, formulation, deliverability (e.g., slow release, prodrugs), or to improve the economy of production, as long as they do not adversely affect the biological activity of the peptide.

Besides substitutions, three particular forms of peptide mimetic and/or analogue structures of particular relevance when designating bioactive peptides, which have to bind to a receptor while risking the degradation by proteinases and peptidases in the blood, tissues and elsewhere, may be mentioned specifically, illustrated by the following examples: Firstly, the inversion of backbone chiral centres leading to D-amino acid residue structures may, particularly at the N-terminus, lead to enhanced stability for proteolytical degradation without adversely affecting activity. An example is given in the paper "Tritriated D-ala$^1$-Peptide T Binding", Smith C. S. et al., Drug Development Res. 15, pp. 371-379 (1988). Secondly, cyclic structure for stability, such as N to C interchain imides and lactams (Ede et al. in Smith and Rivier (Eds.) "Peptides: Chemistry and Biology., Escom, Leiden (1991), pp. 268-270), and sometimes also receptor binding may be enhanced by forming cyclic analogues. An example of this is given in "Conformationally restricted thymopentin-like compounds", U.S. Pat. No. 4,457,489 (1985), Goldstein, G. et al. Thirdly, the introduction of ketomethylene, methylsufide or retroinverse bonds to replace peptide bonds, i.e., the interchange of the CO and NH moieties are likely to enhance both stability and potency. An example of this type is given in the paper "Biologically active retroinverso analogues of thymopentin", Sisto A. et al in Rivier, J. E. and Marshall, G. R. (eds) Peptides, Chemistry, Structure and Biology", Escom, Leiden (1990), pp. 722-773).

The peptides of the invention can be synthesized by various methods which are known in principle, namely by chemical coupling methods (cf. Wunsch, E: "Methoden der organischen Chemiet", Volume 15, Band 1+2, Synthese von Peptiden, thime Verlag, Stutt (1974), and Barrany, G.; Marrifield, R. B.: "The Peptides", eds. E. Gross, J. Meienhofer, Volume 2, Chapter 1, pp. 1-284, Academic Press (1980)), or by enzymatic coupling methods (cf. Widmer, F. Johansen, J. T., Carlsberg Res. Commun., Vol.44, pp. 37-46 (1979), and Kullmann, W.: "Enzymatic Peptide Synthesis", CRC Press Inc. Boca Raton, Fla. (1987), and Widmer, F., Johansen, J. T. in "Synthetic Peptides in Biology and Medicines", eds. Alitalo, K., Partanen, P., Vatieri, A., pp.79-86, Elsevier, Amsterdam (1985)), or by a combination of chemical and enzymatic methods if this is advantageous for the process design and economy.

A cysteine residue may be added at both the amino and carboxy terminals of the peptide, which will allow the cyclization of the peptide by the formation of a disulphide bond.

Any modifications to the peptides of the present invention which do not result in a decrease in biological activity are within the scope of the present invention.

There are numerous examples which illustrate the ability of anti-idiotypic antibodies (anti-Id Abs) to an antigen to function like that antigen in its interaction with animal cells and components of cells. Thus, anti-Id Abs to a peptide hormone antigen can have hormone-like activity and interact specifically with a mediator in the same way as the receptor does. (For a review of these properties see: Gaulton, G. N. and Greane, M. I. 1986. Idiotypic mimicry of biological receptors, Ann. Rev. Immunol. Vol. 4, pp. 253-280; Sege K. and Peterson, P. A., 1978, Use of anti-idiotypic antibodies as cell surface receptor probes, Proc. Natl. Acad. Sci. U.S.A., Vol. 75, pp. 2443-2447).

It is expected from this functional similarity of anti-Id Ab and antigen, that anti-Id Abs bearing the internal image of an antigen can induce immunity to such an antigen. (See review in Hiernaux, J. R., 1988, Idiotypic vaccines and infectious diseases, Infect. Immun., Vol. 56, pp. 1407-1413).

It is, therefore, possible to produce anti-idiotypic antibodies to the peptides of the present invention which will have similar biological activity.

Accordingly, the present invention also provides anti-idiotypic antibodies to the peptides of the present invention, the anti-idiotypic antibody being capable of inhibiting TNF toxicity, but not its binding to the receptor.

The individual specificity of antibodies resides in the structures of the peptide loops making up the Complementary Determining Regions (CDRs) of the variable domains of the antibodies. Since in general the amino acid sequence or the CDR peptides of an anti-Id Ab are not identical to or even similar to the amino acid sequence of the peptide antigen from which it was originally derived, it follows that peptides whose amino acid sequence in quite dissimilar, in certain contexts, can take up a very similar three-dimensional structure. The concept of this type of peptide, termed a "functionally equivalent sequence" or mimotope by Geyson is known. (Geyson, H. M. et al, 1987, Strategies for epitope analysis using peptide synthesis., J. Immun. Methods, Vol. 102, pp. 259-274).

Moreover, the three-dimensional structure and function of the biologically active peptides can be simulated by other compounds, some not even peptidic in nature, but which nevertheless mimic the activity of such peptides. This field is summarized in a review by Goodman, M. (1990), (Synthesis, Spectroscopy and computer simulations in peptide research, Proc. 11th American Peptide Symposium published in Peptides-Chemistry Structure and Biology, pp. 3-29; Eds. Rivier, J. E. and Marshall, G. R. Publisher Escom).

It is also possible to produce peptide and non-peptide compounds having the same three-dimensional structure as the peptides of the present invention. These "functionally equivalent structures" or "peptide mimics" will react with antibodies raised against the peptide of the present invention and may also be capable of inhibiting TNF toxicity.

Accordingly, a further embodiment of the present invention provides a compound the three-dimensional structure of which is similar as a pharmacophore to the three-dimensional structure of the peptides of the present invention, the compound being characterized in that it reacts with antibodies raised against the peptides of the present invention and that the compound is capable of inhibiting TNF toxicity.

More detail regarding pharmacophores can be found in Bolin et al., p. 150, Polinsky et al., p. 287, and Smith et al., p. 485, in Smith and Rivier (eds.) "Peptides: Chemistry and Biology", Escom, Leiden (1991).

All of the molecules (proteins, peptides, etc.) may be produced either by conventional chemical methods, as described herein, or by recombinant DNA methods.

All of the molecules (proteins, peptides, etc.) may be produced either by conventional chemical methods, as described herein, or by recombinant DNA methods.

The invention also provides DNA molecules encoding the ligands according to the invention, vectors containing them and host cells comprising the vectors and capable of expressing the ligands according to the invention.

The host cell may be either prokaryotic or eukaryotic.

The invention further provides DNA molecules hybridizing to the above DNA molecules and encoding ligands having the same activity.

The invention also provides pharmaceutical compositions comprising the above ligands which are useful for treating diseases induced or caused by the effects of TNF, either endogenously produced or exogenously administered.

BRIEF DESCRIPTION OF THE DRAWINGS

FIG. 2 shows an example of the Western blotting analysis technique by which the binding of the antibodies to the constructs shown in FIG. 1 have been determined.

FIGS. 3 & 4 show the competition of synthetic peptides whose sequences contain the region of the epitope recognized by the monoclonal antibodies of the 32 group, or parts of it, with the binding of an antibody of this group to a construct comprising part of TBP-II in which this epitope is present.

FIGS. 5A-5C show the nucleotide (SEQ ID NO:2) and deduced amino acid (SEQ ID NO:3) sequences of the p75 receptor. TBP-II and transmembranal domains are boxed and shaded. The region recognized by the group 32 antibodies is underlined.

FIGS. 11A and 11B show the nucleotide (SEQ ID NO:4 for #70; SEQ ID NO:6 for #32; SEQ ID NO:8 for #57) and deduced amino acid (SEQ ID NO:5 for #70; SEQ ID NO:7 for #32; SEQ ID NO:9 for #57) sequences for the CDR region of the heavy chains of three monoclonal antibodies of the 32 group.

FIG. 12 shows the nucleotide (SEQ ID NO:10) and deduced amino acid (SEQ ID NO:11) sequences for the CDR region of the light chains of monoclonal antibody No. 32.

FIG. 13 shows the amino acid sequence homology between several members of the TNF/NGF receptor family (residues 3-155 of hu p55 TNF-R (SEQ ID NO:12); residues 39-201 of hu p75 TNF-R (SEQ ID NO:13); residues 31-149 of hu FAS (SEQ ID NO:14); residues 3-161 of hu NGF-R (SEQ ID NO:15); residues 25-187 of hu CDw4O (SEQ ID NO:16); and residues 25-164 of rat Ox40 (SEQ ID NO:17)).

DETAILED DESCRIPTION OF THE INVENTION

Figure 1:
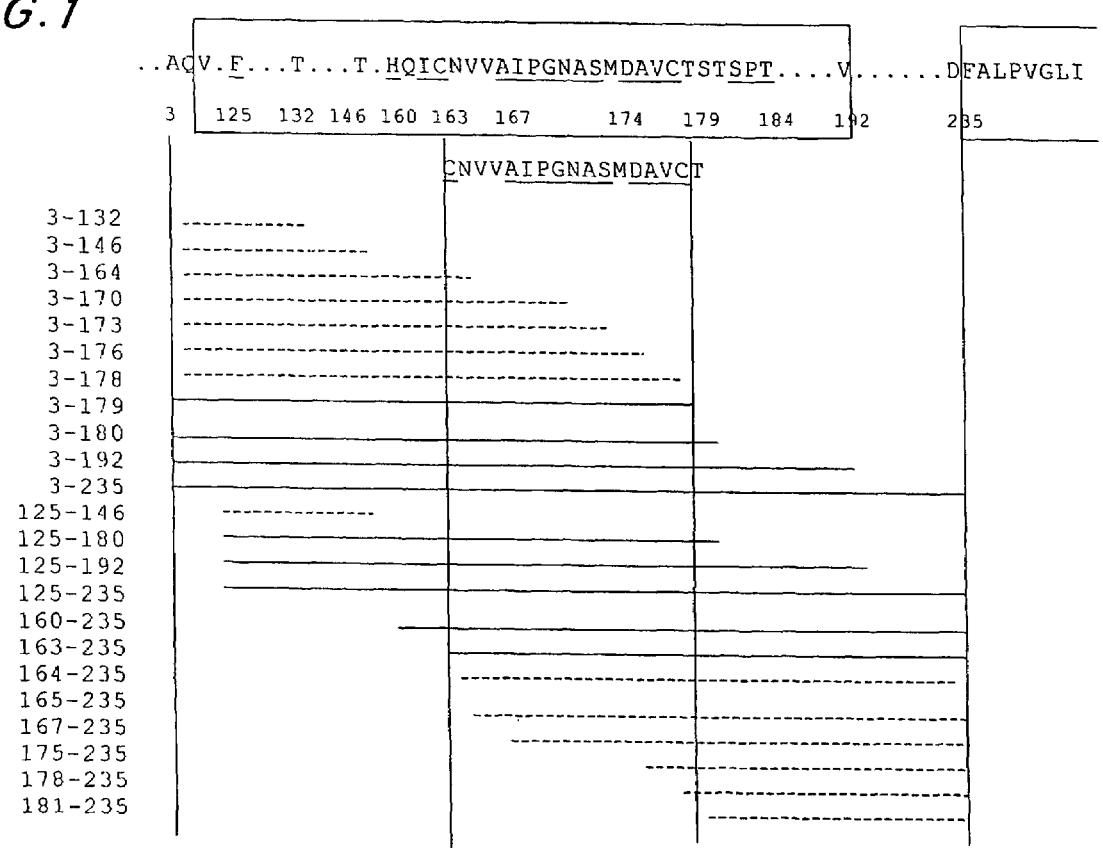
FIG. 1 shows a diagrammatic illustration of the bacterial constructs used for determining the sequence to which antibodies of the 32 group bind. The residues numbered 3 to 235 correspond to residues 25 to 257 of SEQ ID NO:3.
Figure 6:
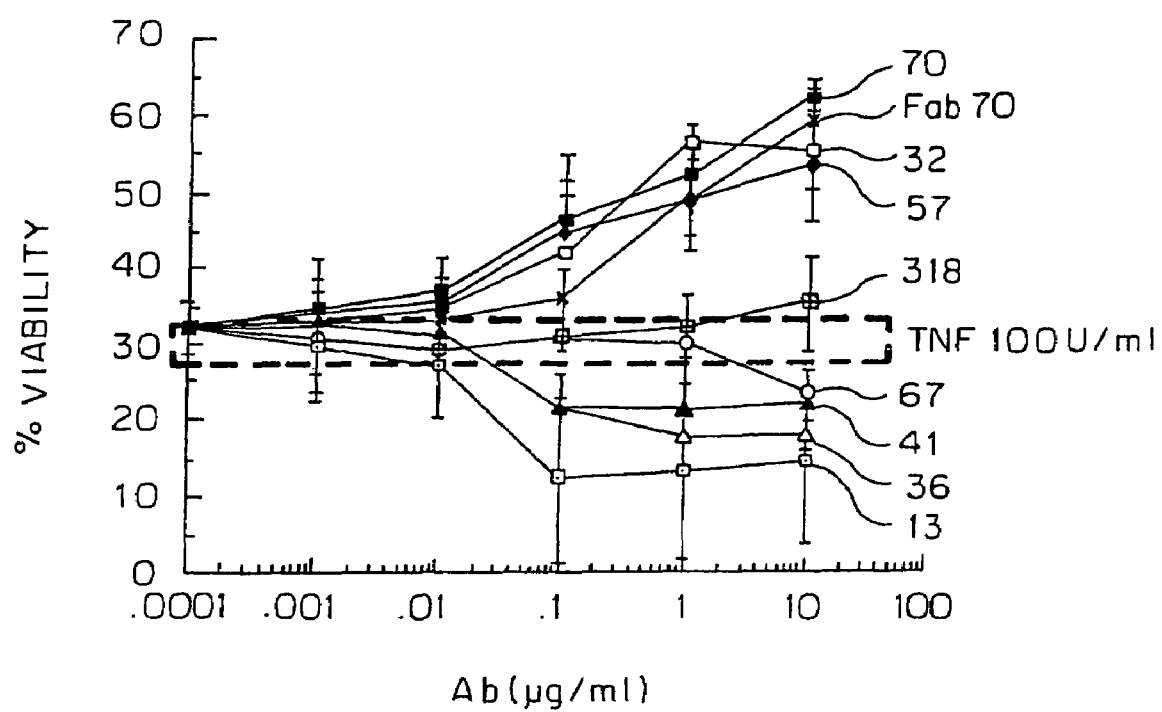
FIG. 6 shows the pattern of protection of HeLa p75.3 cells (as hereinafter defined) from TNF cytotoxicity by different monoclonal antibodies against p75 TNF-R, and fragments thereof.
Figure 7:
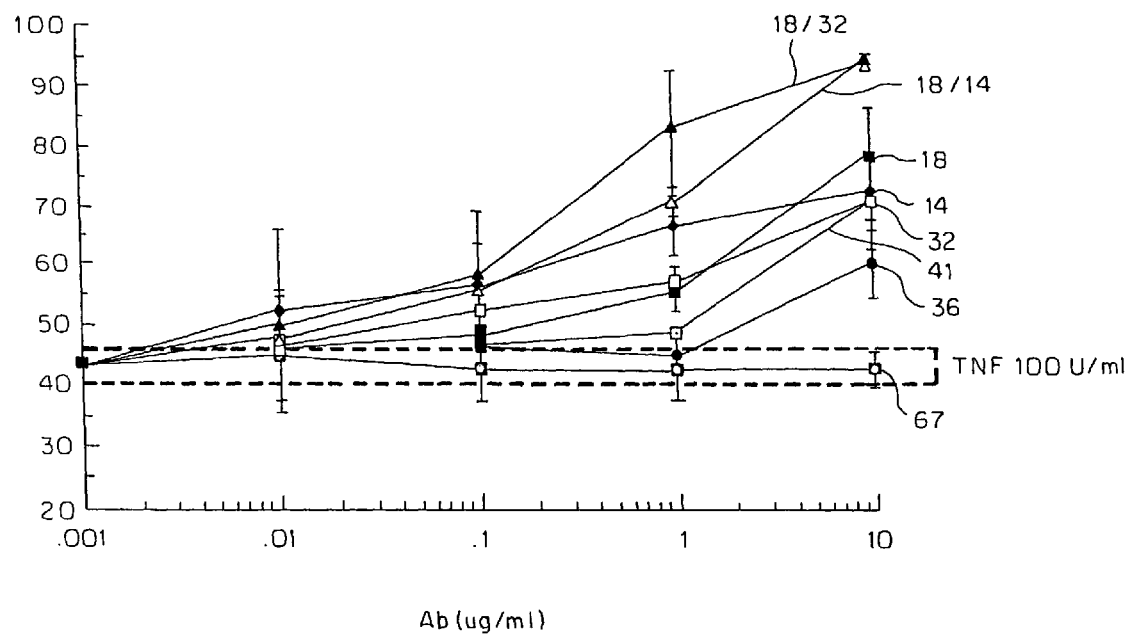
FIG. 7 shows the effects of a monoclonal antibody against TBP-I and several against TBP-I on the extent of killing of U937 cells by TNF.
Figure 8A:
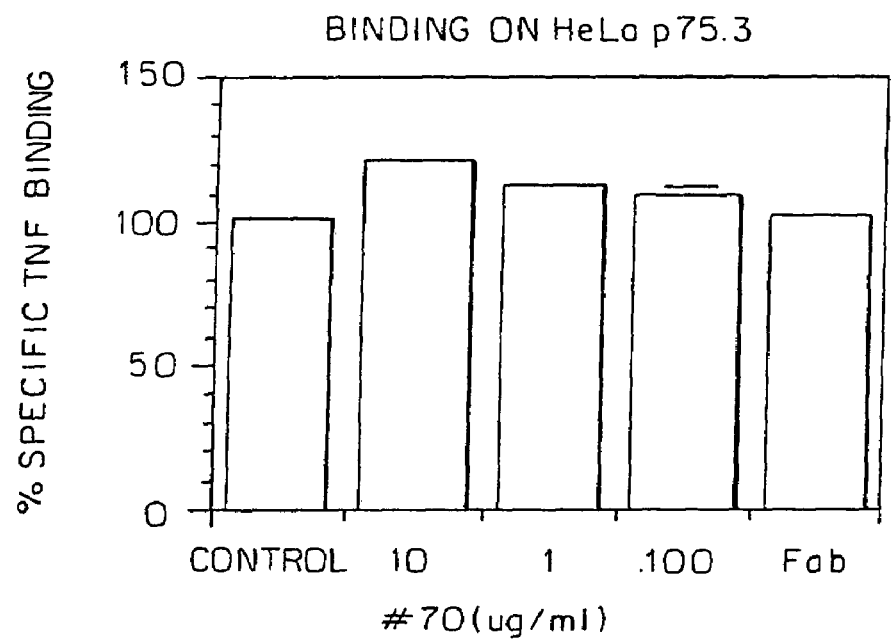
FIGS. 8a and 8b (hereinafter collectively referred to as FIG. 8) show the effects of monoclonal antibody 70 and Fab fragments thereof on the binding of TNF to HeLa p75.3 cells and U937 cells, respectively.
Figure 8B:
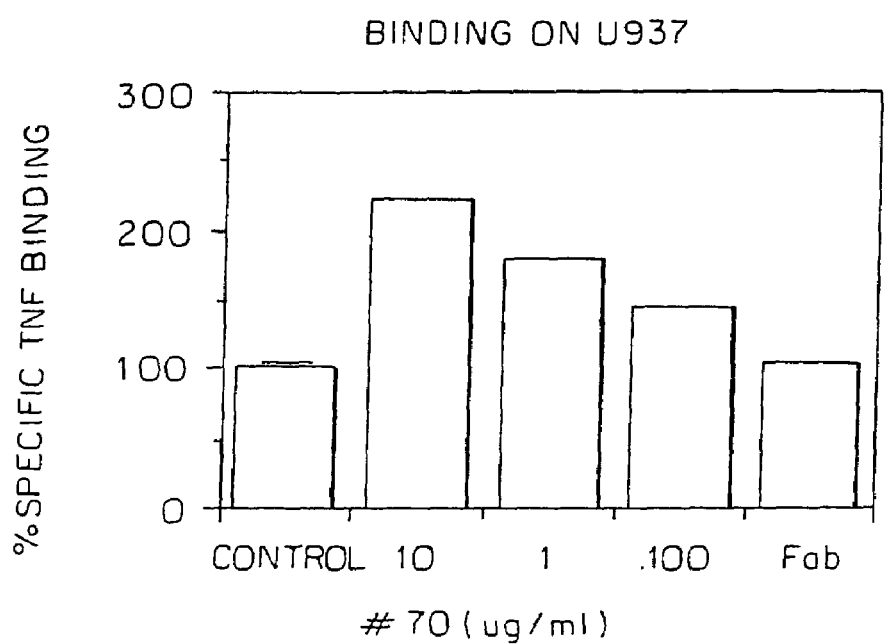
Figure 9A:
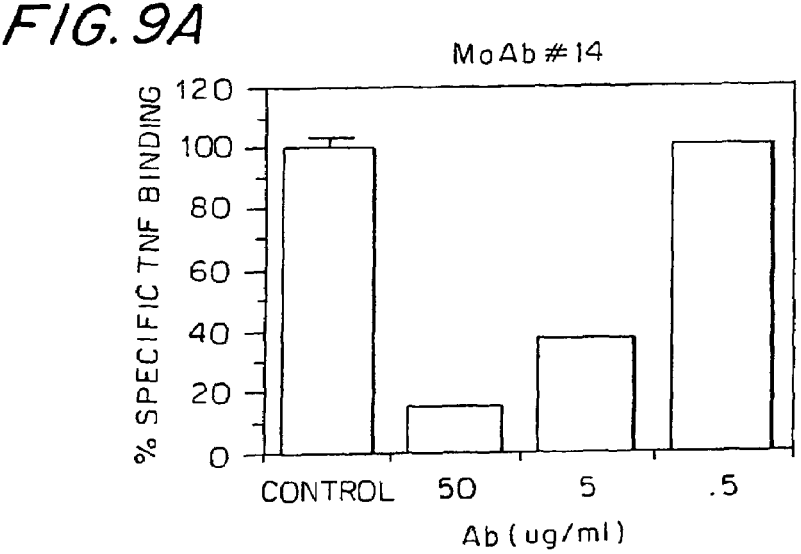
FIGS. 9A-9F (hereinafter collectively referred to as FIG. 9) show comparisons of the effects of the antibody 32 with other antibodies against the p75 TNF-R on TNF binding to HeLa p75.3 cells; namely MoAb #14 (FIG. 9A0, MoAb #32 (FIG. 9B), MoAb #31 (FIG. 9C), MoAb #67 (FIG. 9D), MoAb #36 (FIG. 9E) and Polyanti-stalk Ab (FIG. 9F).
Figure 9B:
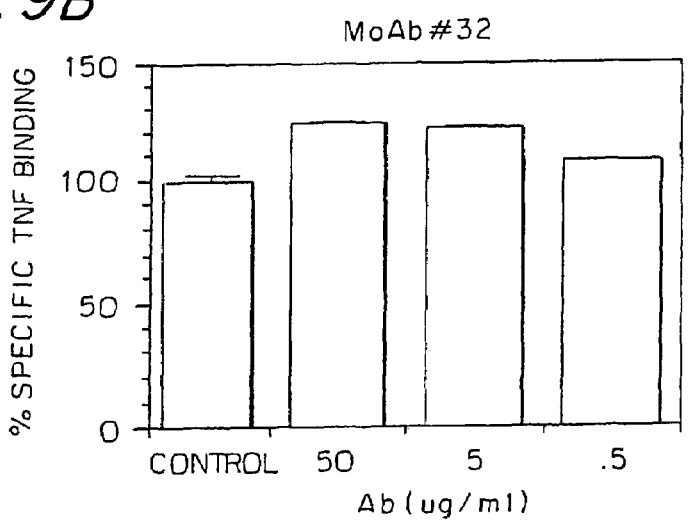
Figure 9C:
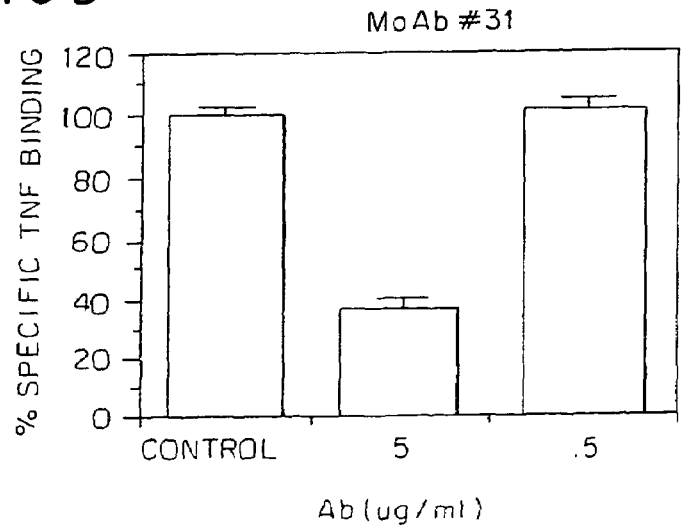
Figure 9D:
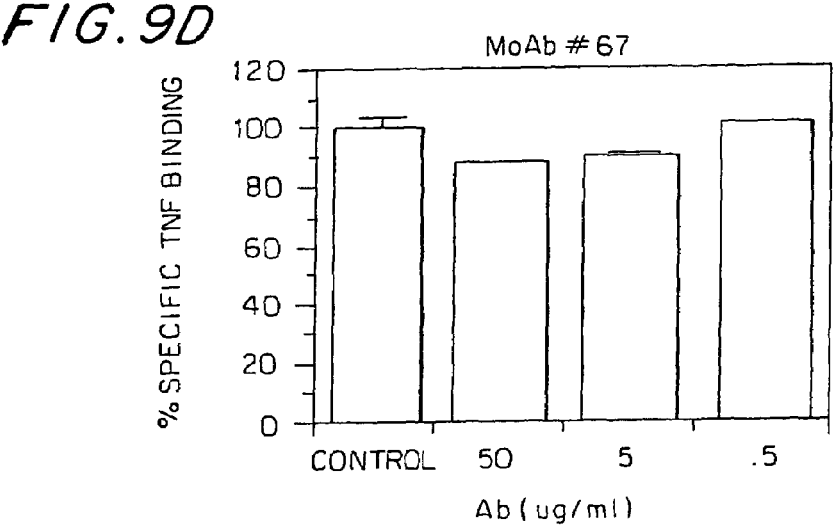
Figure 9E:
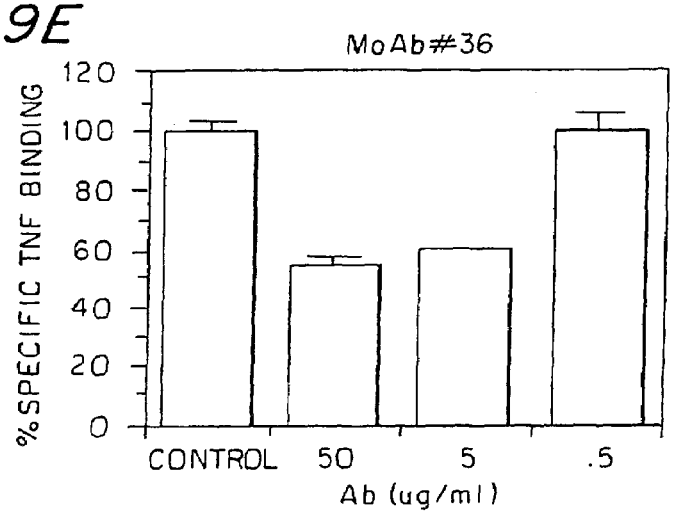
Figure 9F:
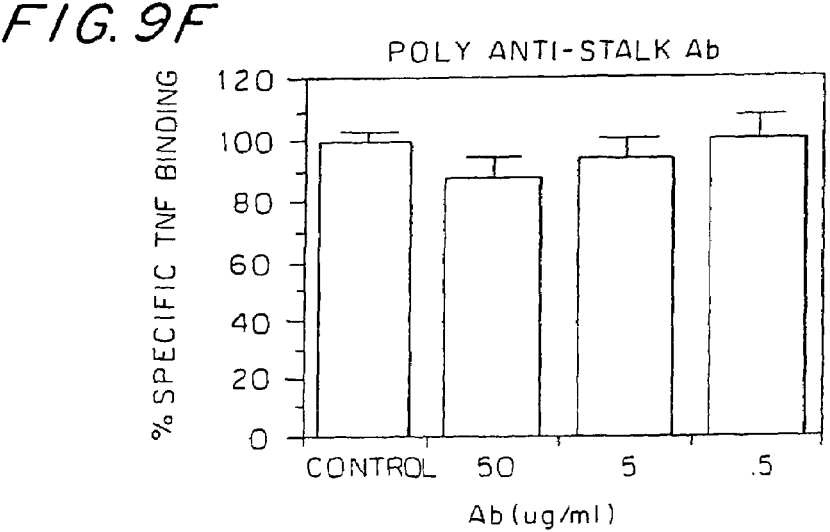
Figure 10:
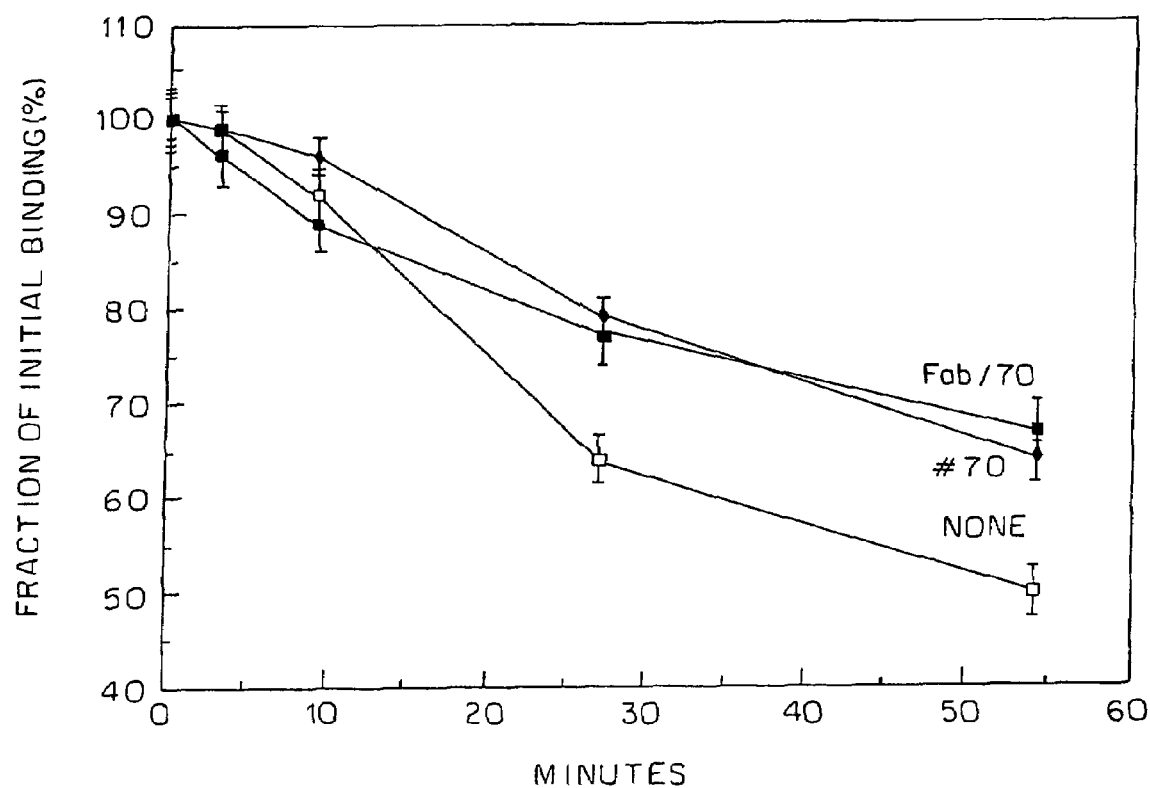
FIG. 10 shows dissociation of TNF from HeLa p75.3 cells in the presence and absence of antibody no. 70 and its monovalent Fab fragment.

TNF, as stated above, is a cytokine which initiates its effect on cell function by binding to two specific cell surface receptors: the p55 and p75 receptors. Binding of antibodies to the extracellular domain of these receptors can interfere with its effect. However, as shown in a number of studies, antibodies binding to the extracellular domain of the receptors can also trigger the effects of TNF by inducing aggregation of the p55 receptors, as well as by inducing aggregation of the p75 receptors. (Engelmann, et al. J. Biol. Chem., Vol. 265, No. 24, pp. 14497-14504, 1990; and unpublished data).

The invention relates to antibodies against TBP-II and to F(ab) fragments thereof, and to salts, functional derivatives and/or active fractions (as defined in parent application Ser. No. 07/930,443 thereof. These antibodies provide a new approach for the modulation of the TNF activity, and may be used both to inhibit and to mimic effects of TNF on specific subsets of cells, depending on the molecular form of the antibodies, specifically on their valence: monovalent forms of the antibodies (e.g., F(ab) fragments) being inhibitory and multivalent forms being able to mimic at least part of the effects of TNF. They are, thus, suitable as pharmaceutical agents both for mimicking and blocking TNF effects on cells.

The functional interaction of the antibodies of the present invention with TBP-II provides also a new diagnostic tool, based on immunoassays such as radioimmunoassay, ELISA etc., for the detection of over- or under-production of TBP-II by cells in the body in certain disorders. Thus, the level of TBP-II in sera of patients with different types of cancer or suffering from autoimmune disorders, such as systemic lupus erythematosus (SLE), can be determined this way. In an inverse approach, antibodies against TBP-II, when produced endogenously in the body, will be measured with the use of purified TBP-II. Detecting such autoantibodies, when formed in certain autoimmune disorders, is of extreme importance, since their ability to mimic or inhibit the effects of TNF surely has far-reaching bearing on the pathological syndromes of said disorders.

The antibodies may be either polyclonal or monoclonal. They may be raised in rabbits, mice or other animals or tissue cultured cells derived thereof or can be products of cells of human origin. They may also be produced by recombinant DNA technology either in a form identical to that of the native antibody or as chimeric molecules, constructed by recombination of antibody molecules of man and animal origins or in other forms chosen to make the antibodies most suitable for use in therapy.

For the preparation of the antibodies, either purified TBP-II or one or more synthetic peptides identical to the known sequence of a fragment thereof, e.g., to the N-terminal protein sequence, may be used to immunize animals. A further possibility is to fuse one of the possible nucleotide sequences coding for a fragment of TBP-II to the gene coding for Protein A, to express the fused Protein A-TBP-II gene in E. coli, to purify the fused protein by affinity chromatography on IgG SEPHAROSE (beaded agarose gel filtration matrix with broad fractionation range and high exclusion limits for the separation of biomolecules; Pharmacia) column and then to use it to immunize animals.

The monoclonal antibodies of the present invention are prepared using conventional hybridoma technique (Kohler et al. (1975) Nature 256:495; Kohler et al. (1976) Eur J Immunol 6:511). After immunization, spleen cells alone or together with lymph node cells of the immunized animals are isolated and fused with a suitable myeloma cell line. After fusion, the resulting hybridoma cells are selectively maintained in RAT medium and then cloned. The hybridoma cells obtained through such a selection are then assayed to identify clones which secrete antibodies capable of binding TBP-II. After identification, the desired clones are grown in bulk, either in suspension culture or in ascitic fluid, by injecting the cells into the peritoneum of suitable host mice. The monoclonal antibodies produced by the hybridomas are then isolated and purified.

As mentioned before, the monoclonal antibodies may also be immobilized and used for the purification of the TBP-II in affinity purification procedure using an immunoadsorbent column.

We have found that certain antibodies binding to one particular region in the p75 receptor are not mimetic but rather inhibitory to the signaling for the cytocidal effect by this receptor. This, in spite or the fact that when binding to this region, these antibodies do not block TNF binding, but rather increase it to some extent.

The present invention reveals that this region recognized by these antibodies which we call the 32 group, is the region extending between the two C-terminal cysteines in the extracellular domain of the p75 receptor, plus an additional amino acid, thr179. This region, for simplicity's sake, is called "cysteine loop" throughout this specification.

The present invention also provides the nucleotide sequences and deduced amino acid sequences in the CDR of the heavy chain of the three antibodies belonging to this group, named 32, 57 and 70. A remarkable similarity between the sequence of amino acids in the CDR of the heavy chain of the 32 and 70 antibodies was found, indicating that the sequence of amino acids in the CDR of the heavy chain of these two antibodies is close to the optimum necessary for binding to the antigen. In addition, the invention also provides the nucleotide sequence and the deduced amino acid sequence of the light chain of antibody 32. Based on these sequences, small molecular weight compounds, peptides or mimetic compounds which will inhibit the function of the p75 receptors can be defined.

In evidence that such small compounds can indeed achieve this and that there is no need for aggregation of receptors, which antibodies are known to be able to do, it was found that also F(ab) monovalent fragments of the antibodies of the 32 group inhibit signaling for toxicity by the p75 receptor when they are triggered by TNF.

In view of these findings, as well as the close similarity of the receptors in this particular family, this invention relates also to agents which bind to the C-terminal cysteine loop in the extracellular domain of the various other members of the TNF/NGF receptor family and modulate the function of the other receptors, similarly to the modulation of the function of TNF. In this receptor family, the localization of cysteine in the extracellular domain and the spacing is highly conserved. Certain members of this family, e.g., CDw40, exhibit particularly high similarity to the p75 receptor. Particularly in such receptors, agents binding to these regions are expected to have effects similar to the effect of the 32 antibodies on the p75 receptor.

As stated above, the ligands according to the invention may comprise proteins, peptides, immunoadhesins, antibodies or other organic compounds.

Proteins may be isolated from cellular extracts, e.g., by ligand affinity purification employing a molecule having an amino acid sequence substantially corresponding to the above-mentioned stretch as ligand.

Peptides may be prepared by synthesizing first target peptides which correspond to the amino acid stretch of the TNF-R found in accordance with the invention to bind the ligands which inhibit the effects of TNF. Thereafter, peptide libraries are screened for other ligands which bind thereto. The peptides which bind to these regions are further screened for those which also bind to TNF-R. Finally, the peptides capably of high affinity binding with both the target peptides and the TNF-R, are screened for the ability of the peptide to perform the desired biological activity.

In a similar manner, a variety of organic molecules, including drugs known for other indications, are screened for their ability to bind to the amino acid stretch found to be critical for inhibiting the effects of TNF.

In addition to the organic molecules, also broth of biological matter, such as bacteria culture products, fungi culture products, eukaryotic culture products and crude cytokine preparations, are screened with the amino acid target peptides described above. Molecules obtained by this screening are then further screened for their ability to perform the desired biological function.

Alternatively, molecules are designed which spatially fit the quaternary structure of the amino acid stretch in the receptor.

The active molecules obtained by the above procedures, insofar as they are biological substances, can also be prepared by biotechnological approaches. In this way, massive production of these molecules will be made possible. Peptides may either be produced by known peptide synthesis methods or using expression vectors containing DNA sequences encoding them. Other molecules, if produced in an enzymatic way, can be made by producing the enzymes involved in the appropriate cultured cells.

Pharmaceutical compositions containing the ligands of the present invention may be employed for antagonizing the effects of TNF in mammals.

Such compositions comprise the ligands according to the invention as their active ingredient. The pharmaceutical compositions are indicated for conditions such as septic shock, cachexia, graft-versus-host reactions, autoimmune diseases such as rheumatoid arthritis, and the like. They are also indicated for counteracting, e.g., an overdose of exogenously administered TNF.

The pharmaceutical compositions according to the invention are administered, depending on the condition to be treated, via the accepted ways of administration. For example, in the case of septic shock, intravenous administration will be preferred. The pharmaceutical compositions may also be administered continuously, i.e., by way of infusion, or orally. The formulation and dose will depend on the condition to be treated, the route of administration and the condition and the body weight of the patient to be treated. The exact dose will be determined by the attending physician.

The pharmaceutical compositions according to the invention are prepared in the usual manner, for example, by mixing the active ingredient with pharmaceutically and physiologically acceptable carriers and/or stabilizers and/or excipients, as the case may be, and are prepared in dosage form, e.g. by lyophilization in dosage vials.

As used herein the term "muteins" refers to analogs of the proteins, peptides and the like in which one or more of the amino acid residues of the protein found to bind are replaced by different amino acid residues or are deleted, or one or more amino acid residues are added to the original sequence, without changing considerably the activity of the resulting product. These muteins are prepared by known synthesis and/or by site-directed mutagenesis techniques, or any other known technique suitable therefor.

The term "fused protein" refers to a polypeptide comprising the ligands or a mutein thereof fused with another protein which has an extended residence time in body fluids. The ligands may thus be fused to another protein, polypeptide or the like, e.g., an immunoglobulin or a fragment thereof.

The term "salts" herein refers to both salts of carboxyl groups and to acid addition salts of amino groups of the ligands, muteins and fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein cover derivatives of the ligands and their fused proteins and muteins, which may be prepared from the functional groups which occur as side chains on the residues or the N- or C-terminal groups, by means known in the art, and are included in the invention as long as they remain pharmaceutically acceptable, i.e., they cannot destroy the activity of the ligand and do not confer toxic properties on compositions containing it. These derivatives may, for example, include polyethylene glycol sidechains which may mask antigenic sites and extend the residence of the ligands in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl groups (for example, that of seryl or threonyl residues) formed with acyl moieties.

The invention is illustrated by the following non-limiting examples:

EXAMPLE 1

Monoclonal Antibodies to TBP-II

Production of the Monoclonal Antibodies

Female Balb/C mice (8 weeks old) were injected with 1 μg purified TBP-II in an emulsion of complete Freund's adjuvant into the hind foot pads, and three weeks later, subcutaneously into the back in incomplete Freund's adjuvant. The other injections were given in weekly intervals, subcutaneously in PBS. Final boosts were given 4 days (i.p.) and 3 days (i.v.) before the fusion with 9.0 μg of TBP-I in PBS. Fusion was performed using NSO/Mr cells and lymphocytes prepared from both the spleen and the local lymphocytes of the hind legs as fusion partners. The hybridomas were selected in DMEM, supplemented with HAT, 15% horse serum and gentamycin 2 μg/ml. Hybridomas that were found to produce antibodies to TBP-1 were subcloned by the limiting dilution method and injected into Balb/C mice that had been primed with pristane for the production of ascites. Immunoglobulins were isolated from the ascites by ammonium sulfate precipitation (50% saturation) and then dialyzed against PBS containing 0.02% azide. Purity was approximately 60% as estimated by analysis on SDS-PAGE and staining with Coomassie blue. The isotypes of the antibodies were defined with the use of a commercially available ELISA kit (Amersham, U.K.).

Several positive clones were obtained, subcloned for further studies and characterized. Some of the isolated subclones with their isotype and binding of TBP-II in inverted RIA are listed in Table I.

TABLE I

Subclones Producing Monoclonal Antibodies to TBP-II

| Clone Number | Screening with iRIA [CPM] | Screening of subclone with iRIA [CPM] | Isotype |
|---|---|---|---|
| 13.11 | 31800 | 31000 | $IgG_1$ |
| .12 | | 31500 | $IgG_1$ |
| .13 | | 31100 | $IgG_1$ |
| 14.1 | 15300 | 15400 | $IgG_{2a}$ |
| .6 | | 16200 | $IgG_{2a}$ |
| .7 | | 15300 | $IgG_{2a}$ |
| 20.2 | 12800 | 14200 | $IgG_{2b}$ |
| .5 | | 14300 | $IgG_{2b}$ |
| .6 | | 14800 | $IgG_{2b}$ |
| 22.7 | 20400 | 20000 | $IgG_1$ |
| .8 | | 19300 | $IgG_1$ |
| 27.1 | 1800 | 27000 | $IgG_{2a}$ |
| .3 | | 25000 | $IgG_{2a}$ |
| .9 | | 28000 | $IgG_{2a}$ |
| 32.4 | 11315 | 10900 | $IgG_{2b}$ |
| .5 | | 10700 | $IgG_{2b}$ |
| .6 | | 11200 | $IgG_{2b}$ |
| 33.1 | 18400 | 11400 | $IgG_1$ |
| .3 | | 10500 | $IgG_1$ |
| .4 | | 14800 | $IgG_1$ |
| 36.1 | 27500 | 26600 | $IgG_{2a}$ |
| .5 | | 24900 | $IgG_{2a}$ |
| .6 | | 24900 | $IgG_{2a}$ |
| 41.3 | 13800 | 18100 | $IgG_1$ |
| .7 | | 18100 | $IgG_1$ |
| .10 | | 18800 | $IgG_1$ |
| 67.1 | 16800 | 10900 | $IgG_{2a}$ |
| .16 | | 10800 | $IgG_{2a}$ |
| .17 | | 10900 | $IgG_{2a}$ |
| 70.2 | 15100 | 5100 | $IgG_{2a}$ |
| .3 | | 5200 | $IgG_{2a}$ |
| .4 | | 5300 | $IgG_{2a}$ |
| 77.2 | 15300 | 11800 | $IgG_{2b}$ |
| 78.9 | 25300 | 21400 | $IgG_{2a}$ |
| 82.1 | 17600 | 25900 | $IgG_1$ |
| .4 | | 25700 | $IgG_1$ |
| .10 | | 26400 | $IgG_1$ |
| 86.2 | 8800 | 12200 | $IgG_{2b}$ |
| .5 | | 12600 | $IgG_{2b}$ |
| .11 | | 12800 | $IgG_{2b}$ |
| 19.6 | | 29700 | $IgG_{2a}$ |
| .9 | | 28900 | $IgG_{2a}$ |

Hybridomas TBP-II 13-12 and TBP-II 70-2 were deposited with the Collection Nationale de Cultures de Microorganismes (CNCM), Institut Pasteur, 25, rue du Docteur Roux, 75724 Paris CEDEX 15, France on Mar. 12, 1990, and were assigned No. I-929 and No. I-928. respectively. Hybridoma 32-5 was deposited with the CNCM on September 1, 1993, and assigned No. I-1358. Another clone producing monoclonal antibodies to TBP-II is hybridoma 57-1,which was deposited with the CNCM on Apr. 23, 1996, and assigned No. I-1696.

EXAMPLE 2

Inverted Radioimmunoassay (iRIA) for the Detection of the Monoclonal Antibodies to TBP-II This assay was used for estimating the level of the anti-TBP antibodies in the sera of the immunized mice and for screening for the production of the antibodies by hybridomas. PVC, 96-well microtiter plates (Dynatech 1-220-25) were coated for 12 hr at 4° C. with affinity purified goat anti mouse F(ab) immunoglobulins (Biomakor, Israel 10 μg/ml in PBS containing 0.02: $NaN_3$), then blocked for 2 hr at 37° C. with 0.52 BSA in PBS supplemented with 0.05% TWEEN 20 (polyoxyethylene sorbitan monolaurate; Sigma) and 0.02% $NaN_3$ (blocking buffer) and washed 3 times with PBS containing 0.05% TWEEN 20 and 0.02% $NaN_3$ (washing buffer). Serum samples, in serial dilutions, or samples of hybridoma growth media (50 µl) were applied into the wells for 2 hr at 37° C. The plates were rinsed with washing buffer and $^{125}$I-labelled TBP-I (10,000 cpm, in blocking buffer) was applied into the wells. After further incubation of 2 hr at 37° C., the plates were washed and the amount of label which bound to individual wells was determined in the gamma-counter.

EXAMPLE 3

The Use of Anti-TBP-II Antibodies for Affinity Chromatography

Antibodies against TBP-II can be utilized for the purification of TBP-II by affinity chromatography, according to the following procedure. The monoclonal antibodies for affinity chromatography were selected by testing their binding capacity for the radiolabeled antigen in a solid phase radio immunoassay. Ascites from all hybridomas was purified by ammonium sulfate precipitation at 50% saturation followed by extensive dialysis against PBS. PVC 96-well plates were coated with the purified McAbs, and after blocking the plates with PBS containing 0.5% BSA, 0.05% TWEEN 20 (Sigma) and 0.02% $NaN_3$, the wells were incubated with 50,000 cpm $^{125}$I-TNF for 2 hr at 37° C., then washed and the radioactivity which had bound to each well was quantitated in the gamma-counter. The antibodies with the highest binding capacity were examined for their performance in immunoaffinity chromatography.

Polyacryl hydrazide agarose was used as resin to immobilize the antibodies. The semipurified immunoglobulins were concentrated and coupled to the resin as specified by Wilchek and Miron, *Methods in Enzymology* 34:72-76, 1979. Three monoclonal antibodies against TBP-I, clones 16, 20, and 34 were tested in these experiments. Antibody columns of 1 ml bed were constructed. Before use, all columns were subjected to 10 washes with the elusion buffer, each wash followed by neutralization with PBS. Then the columns were loaded with 120 ml of concentrated urinary proteins in PBS with 0.02% $NaN_3$. The flow rate of the columns was adjusted to 0.2 to 0.3 ml per minute. After loading, the columns were washed with 50 ml PBS and then eluted with a solution containing 50 mM citric acid, pH 2.5, 100 mM NaCl and 0.02% $NaN_3$. Fractions of 1 ml were collected. Samples of the applied urinary proteins, the last portion of the wash (1 ml) and of each elusion fraction (8 fractions of 1 ml per column) were taken and tested for protein concentration and activity in the bioassay for T3P-II. According to the protein measurements before and after coupling of the antibodies to hydrazide agarose, the amounts of immunoglobulin bound to the columns ranged from 7 to 10 mg/ml agarose. All protein measurements were done according to a micro-flurescamin method in comparison to a standard solution containing 100 µg BSA/ml (Stein, S. and Moschera. J., *Methods Enzymol.* 79:7-16, 1981).

EXAMPLE 4

Determination of TBP-II Using Anti-TBP-II Antibodies

The levels of TBP-II in the sera of healthy individuals, patients with cancer or systemic lupus erythematosus (SLE) and of pregnant women at term were determined by an ELISA method employing a monoclonal antibody to TBP-II coating the plates. 50 µl of each sample was added and after a 2.5 hr incubation at 37° C. the wells were washed with a solution of PBS, TWEEN 0.05% and sodium azide 0.02%, after which a rabbit anti-TBP-II polyclonal antibody was added for 2.5 hr at 37° C. Then the wells were washed again (no azide) and goat anti-rabbit horseradish peroxidase-coupled antibody was added for 2 hr. Following this incubation, and washing, an ABTS buffer was added and optical density (O.D.) read 30 min. later at 600 nm.

The normal levels of TBP-II in human serum of healthy individuals as determined by the ELISA method are 1.48±0.46 ng/ml.

In the sera of 46 patients with Systemic Lupus Erythematosus (SLE), the TBP-II levels were 4.04±3.75 ng/ml, a value highly significant compared to the normal levels (p<0.001). 29 out of the 46 patients with SEE had a TBP-II level higher than the mean 2SD of normal values. A highly significant correlation was found between the TBP-II levels and the disease activity index developed by Symmonds, D. P. M. et al, Quarterly J. of Med, (1988), Vol. 69, pp. 927-937: r=0.62, p<0.001. A similar correlation was found between TBP-II and the classical marker of SLE activity, the anti-DNA antibodies (r=0.64, p<0.001) and between a major clinical manifestation of SLE activity, i.e., joint pains and TBP-II (r=0.54, p<0.001).

These results indicate that TBP-II may be useful as a sensitive marker of disease activity and a predictor of exacerbations in SLE patients, and thus may be useful in monitoring immune activation related to disease activity in these patients as well as in patients with other autoimmune diseases.

By the above ELISA method, the TBP-II levels in sera of patients with different types of cancer, were examined. In 20 out of 34 patients (58.8%) with different types of cancer, the TBP-II levels were above the normal mean ±2SD. The difference between the TBP-II of cancer patients (4.16±4.08 ng/ml) and healthy controls (1.48±0.46 ng/ml) was highly significant statistically (p<0.001)

These results indicate that TBP-II may prove a useful and universal marker of different types of cancer and may be applied in early detection of this condition. After cancer resection, normalization of TBP-II levels may be a marker of cure of the disease. An increase in TBP-II, after initial normalization, may be an early and sensitive universal marker of disease relapse.

14 pregnant women at term with eclampsia or pre-eclampsia had statistically significant higher TBP-II levels (2.91±0.96 ng/ml) than 16 normotensive pregnant women (1.58±0.52) as determined by the ELISA method (p<0.001).

EXAMPLE 5

Epitope Mapping of TBP-II by Cross Competition Analysis with Monoclonal Antibodies (mAbs) to TBP-II PVC 96-well microtiter plates were coated as described above, with purified mAbs to TBP-II (25 µg/ml). Following rinsing and blocking, samples of $^{125}$I-labelled T3P-II (100, 000 cpm per well) which had been preincubated for 2 hr, at 37° C. with the same or a different monoclonal antibody to TBP-II (at 1 µg/ml) were put into the wells; the plates were incubated overnight at 4° C., washed and the radioactivity bound to each well was determined by gamma counting. The results are expressed as percent of the control values (TBP-II binding in the absence of competing mAbs).

The results are depicted in Table II. The monoclonal antibodies are indicated by the clone numbers in the first row and ~n left column. Low percent binding values indicate that the two antibodies compete for each other's epitope on TBP-II, while higher values indicate that they bind to different epitopes. Non-competitive antibodies are suitable for use in double-sandwich ELISA, e.g., clones 13 and 70.

A bacterially produced construct corresponding to amino acids 3 to 180 of the p75 TNF-R (p75 construct in FIG. 3, corresponding to residues 25 to 202 of SEQ ID NO:3) was applied, at the indicated concentrations, to PVC plates pre-

TABLE II

Cross Competition Analysis with Monoclonal Antibodies to TBP II

| | | Solid Phase Antibodies | | | | | | | | | | | | | | |
|---|---|---|---|---|---|---|---|---|---|---|---|---|---|---|---|---|
| | | 13 | 14 | 19 | 20 | 22 | 27 | 32 | 33 | 36 | 41 | 67 | 70 | 77 | 78 | 82 | 86 |
| Competitor Antibody | 13 | 4 | 64 | 53 | 73 | 31 | 51 | 161 | 35 | 177 | 72 | 131 | 128 | 77 | 102 | 50 | 101 |
| | 14 | 119 | 20 | 90 | 13 | 13 | 84 | 156 | 11 | 132 | 173 | 134 | 113 | 14 | 70 | 89 | 179 |
| | 19 | 103 | 28 | 7 | 19 | 11 | 5 | 144 | 11 | 144 | 133 | 179 | 123 | 18 | 5 | 85 | 126 |
| | 20 | 119 | 17 | 93 | 14 | 10 | 88 | 149 | 9 | 135 | 170 | 137 | 135 | 16 | 70 | 101 | 181 |
| | 22 | 109 | 26 | 94 | 22 | 13 | 82 | 128 | 12 | 115 | 164 | 136 | 114 | 17 | 68 | 98 | 167 |
| | 27 | 106 | 23 | 11 | 27 | 14 | 8 | 145 | 17 | 152 | 133 | 196 | 136 | 24 | 8 | 82 | 125 |
| | 32 | 150 | 267 | 150 | 291 | 156 | 186 | 14 | 163 | 139 | 200 | 205 | 18 | 294 | 143 | 103 | 226 |
| | 33 | 115 | 19 | 98 | 23 | 16 | 86 | 133 | 12 | 118 | 156 | 120 | 114 | 24 | 78 | 90 | 155 |
| | 36 | 155 | 262 | 168 | 271 | 144 | 185 | 167 | 158 | 12 | 169 | 223 | 135 | 265 | 158 | 93 | 150 |
| | 41 | 117 | 119 | 119 | 118 | 101 | 109 | 118 | 76 | 93 | 9 | 179 | 107 | 106 | 111 | 8 | 9 |
| | 67 | 112 | 138 | 125 | 141 | 125 | 157 | 136 | 107 | 138 | 213 | 30 | 117 | 120 | 127 | 106 | 236 |
| | 70 | 150 | 246 | 150 | 255 | 145 | 166 | 4 | 162 | 166 | 217 | 204 | 6 | 232 | 132 | 107 | 234 |
| | 77 | 121 | 18 | 98 | 15 | 13 | 78 | 148 | 11 | 145 | 184 | 142 | 132 | 18 | 66 | 103 | 184 |
| | 78 | 118 | 20 | 9 | 26 | 10 | 6 | 153 | 13 | 157 | 137 | 183 | 131 | 19 | 6 | 94 | 172 |
| | 82 | 107 | 110 | 130 | 116 | 112 | 121 | 128 | 89 | 90 | 8 | 162 | 102 | 121 | 113 | 8 | 7 |
| | 86 | 122 | 181 | 125 | 166 | 126 | 129 | 131 | 120 | 86 | 18 | 253 | 109 | 152 | 125 | 20 | 17 |
| | 100% value | 31582 | 3958 | 2057 | 5437 | 2947 | 17395 | 25923 | 3525 | 6368 | 8042 | 4368 | 24113 | 5887 | 22222 | 11608 | 9703 |

EXAMPLE 6

Determination of the Region of the p75 Receptor which is Recognized by the Group 32 Antibodies We have now prepared a number of constructs by expression in *E. coli* and the complete list of constructs examined, as well as their relationship to the structure of the soluble p75R are shown in FIG. 1. Constructs recognized by the antibodies of the 32 group are listed in bold numbers and illustrated as solid lines. Those not reacting with these antibodies are listed in thin numbers and illustrated by broken lines. All constructs are identified by their N- and C-terminal amino acid residues. It can, therefore, be concluded that the epitope recognized by antibody no. 32 maps between amino acids 163-179, which corresponds to residues 185-201 of SEQ ID NO:3.

FIG. 1, above the diagrammatic illustration of the constructs, shows the amino acid sequence of part of the p75 TNF-R, the regions corresponding to the soluble form of the receptor and the transmembranal region being boxed. Amino acid residues conserved between man and mouse are underlined.

EXAMPLE 7

Competition for Binding to the Extracellular Domain of the p75 TNF-R Between Group 32 Antibodies and Synthetic Peptides A number of synthetic peptides whose sequences correspond to various parts of the region on the TNF-R suspected to be the group 32 epitope were synthesized (residues 160-179, 162-179, 163-179, 165-179 and 167-179 corresponding to residues 182-201, 184-201, 185-201, 187-201 and 189-201 of SEQ ID NO:3, respectively). The peptides were examined in an ELISA test for their ability to compete for the binding to the antibodies of the 32 group.

coated with antibody 32 followed by application of rabbit antiserum to TBP-II (p75 soluble TNF-R). The amount of rabbit antiserum bound to the plate was determined by applying goat antiserum against rabbit immunoglobulin, coupled to horseradish peroxidase and enzymatic assessment of the amount of goat immunoglobulin bound to the plate. FIG. 3 shows the data of an experiment in which a synthetic peptide corresponding to amino acid residues 163 to 179 was found to compete for the binding.

FIG. 4 shows the data of an experiment in which a fusion protein of maltose binding protein (TBP) with the sequence of amino acids extending from 125 to 192 of the p75 receptor (corresponding to residues 147-214 of SEQ ID NO:3) was used to coat PVC plates at a concentration or 10 μg/ml, then the No. 32 McAb was applied at a concentration of 2 μg/ml together with the indicated concentrations of different peptides:

DW16—amino acids 165-179 (corresponding to residues 187 to 201 of SEQ ID NO:3)

DW18—amino acids 163-179 (corresponding to residues 185 to 201 of SEQ ID NO:3)

DW19—amino acids 162-179 (corresponding to residues 184 to 201 of SEQ ID NO:3)

DW21—amino acids 160-179 (corresponding to residues 160 to 179 of SEQ ID NO:3)

Thereafter, the reaction was developed by adding goat anti-mouse coupled to horseradish peroxidase. As shown in FIG. 4, marked inhibition of fusion protein recognition by monoclonal antibody No. 32 was observed only with the three peptides covering the whole epitope.

EXAMPLE 8

Mutational Study of the 32 Epitope

Replacing cysteine 178 with alanine in a recombinant peptide whose sequence corresponds to amino acids 3 to 181 (SEQ ID NO:5), made this protein unrecognizable by the 32 group antibodies. This finding suggests that in order to be recognized by these antibodies, the two cysteines in the group 32 epitope region must be free to interact with each other; i.e., that the structure recognized by the antibodies is a loop. In support of this notion, we found that reduction of the peptide with dithiothreithol prior to SDS PAGE and Western blotting analysis somewhat decreased the effectivity of its recognition by the 32 group antibodies, and reduction by dithiothreithol followed by alkylation with iodoacetimide made it completely unrecognizable by the antibodies.

EXAMPLE 9

Effects of Various Antibodies and Fragments Thereof on TNF Toxicity

In order to compare the function of the 32 group antibodies, not only to antibodies which bind to the receptor upstream to the 32 epitope region (as most of the anti-TBP-II antibodies are expected to), but also to antibodies that bind to the receptor downstream to that epitope region, we immunized mice with a chimeric construct corresponding to the region extending downstream to the 32 epitope (amino acids 181 to 235 which corresponds to residues 203 to 257 of SEQ ID NO:3; the "stalk" region), linked to MBP. The rabbits developed antibodies which bound to the chimera with which they were immunized as well as to the intact p55 TNF receptor. These antibodies were affinity purified by binding to the chimeric protein, linked to an AFFI-GEL 10 column (crosslinked agarose matrix with N-hydroxysuccinimide as functional group; BioRad), and tested for effect on TNF function and binding. (The affinity purified antibody preparation was termed "318".)

All monoclonal anti-TBP-II antibodies as well as the affinity purified anti-stalk antibodies were tested for effect on TNF toxicity in clones of the epitheloid HeLa cells which were made to over-express the p75 receptors (by their transfection with the p75 receptor's cDNA. We called the particular over-expressing clone used in the experiments presented here, HeLa p75.3). The only antibodies found to inhibit TNF function were the antibodies of the group 32 epitope; that, in spite of the fact that they do not inhibit, but somewhat increase TNF binding to the receptor (FIGS. 8 and 9). Two of the other anti-TBP-II antibodies (No. 67 of FIGS. 6 and 9 and number 81) had very little effect on TNF binding to the receptor or on TNF toxicity. All other monoclonal anti-TBP-II antibodies somewhat potentiated the cytocidal effect of TNF even though competing with TNF binding (e.g., antibody 36 of FIGS. 6 and 9). The "anti-stalk" antibodies had very little effect on TNF binding or function (FIGS. 6 and 9). Applying the anti-stalk antibodies on the cells together with antibodies of the 32 group did not interfere with the inhibitory effect of the latter on TNF function.

The same panel of antibodies was tested for effect on the killing of the myelocytic U937 cells by TNF. As opposed to the mimetic effect of anti-TNF receptor antibodies in the HeLa cells, neither anti-p55 nor anti-p75 receptor antibodies were found to be mimetic to the cytocidal effect of TNF on the U937 cells under the conditions of the experiment carried out. Having no ability to mimic the effect of TNF, all monoclonal antibodies which compete for TNF binding either to the p75 receptor, (e.g., antibodies 14, 31 and 36 of FIG. 9) or to the p55 receptor (e.g., antibody number 18 of FIG. 7) are inhibitory to the TNF effects. Antibodies which had no effect on TNF binding to the receptors (e.g., number 67 of FIG. 9) had no effect on TNF function (FIG. 6). The 32 group antibodies were unique in having an ability to inhibit TNF function in this cell without having any inhibitory effect on TNF binding. The antibodies actually enhanced the binding of TNF to these cells, much more so than in the HeLa 075.3 cells (FIG. 8). The inhibitory effect of the 32 group antibodies was additive to that of antibodies which block TNF binding to the p55 receptor (e.g., the combination 18/32 in FIG. 7).

EXAMPLE 10

Effect of group 32 Antibodies and Fab Monovalent Fragments Thereof on the Dissociation of TNF from the TNF-Rs In order to explore the mechanism by which the 32 group antibodies cause an increase in TNF binding, we compared the rate of TNF dissociation from HeLa p75.3 cells in the presence and absence of these antibodies.

Radiolabeled TNF was added to confluent HeLa p75.3 cells and the cells were incubated for 2 hr on ice. Unbound ligand was washed away and 1 ml of binding buffer containing 500 ng/ml of cold TNF was applied into quadruplicate wells for the indicated periods of time on ice. Thereafter, the wells were washed once again with cold PBS, and the amount of residual ligand was determined by measuring radioactivity of cells detached from plates by incubation with PBS/EDTA solution. The antibodies were applied throughout the assay at a concentration of 10 μg/ml.

As illustrated in FIG. 10, both these antibodies as well as their F(ab) monovalent fragments caused a decrease in the rate of TNF dissociation from the receptors. Besides providing a possible explanation for the way in which these antibodies affect THF binding to its receptors, this finding indicated an additional application for this effect. Soluble forms of the p75 TNF-Rs or of the p55 receptor or of any other member of the TNF/BGF receptor family in which a conformational change as that imposed by the 32 group antibody will occur, will serve as better inhibitors of the respective agonist.

EXAMPLE 11

Determination of Nucleotide Sequences and Deduced Amino Acid Sequences in the CDR of the Heavy Chains of Monoclonal Antibodies 32, 57 and 70 (Group 32 Antibodies) and in the CDR of the Light (Kappa) Chain of Antibody 32

In order to determine the nucleotide sequences of the CDR of the heavy chains of antibodies 32, 57 and 70, total RNA was isolated by the Promega protocol from the respective hybridoma cells, with the use of guanidinium thioisocyanate. First strand cDNA synthesis on this RNA was performed with the use of AMV reverse transcriptase and either oligo(dT)15-18 or an oligonucleotide complementary to the constant region of the heavy chain of murine IgG as a primer. The cDNA was used as a template for PCR, applying a partially degenerate 5'-Primer. 40 cycles of PCR were carried out. PCR products with the size of about 350 bp were purified electrophoretically and cloned into the Bluescript vector. Clones having inserts of the right size were sequenced. Double-stranded cDNA or the CDR region or the light chain or antibody no. 32 was synthesized in a similar manner.

The nucleotide sequences obtained by the dideoxy chain termination method, and the amino acid sequences deduced therefrom are shown in FIGS. 11 and 12. The CDR1, 2 and 3 regions are underlined.

EXAMPLE 12

Preparation of scFv of the 32 Group Antibodies

The cloned variable regions of the heavy and light chains of the monoclonal antibodies of the 32 group are linked with a linker of 15 amino acid length and introduced into a commercial expression vector. The vector contains a promoter, e.g., lac, a leader sequence, e.g., pel-B, as well as a, sequence encoding a small peptide ("tag" peptide) against which a monoclonal antibody is commercially available. The plasmid is now introduced into *E. coli* and the bacteria are grown to O.D. 0.5-1.0. Expression of scFv is induced by addition of IPTG and growth is continued for another 6-24 furs. The soluble scFv-tag complex is then isolated from the culture medium by immunoaffinity purification using the monoclonal antibody against the tag and then purified on a metaloaffinity column.

Any scFv accumulating within the bacteria is purified by isolating and repeatedly washing the inclusion bodies, followed by solublization by, e.g., urea or guanidinium and subsequent renaturation.

Alternative possibilities are employing an oligohistidine as the tag, using a stronger promoter instead of lac, i.e., T7, constructing the vector without the leader sequence or introducing a sequence encoding a "tail" of irrelevant sequences into the vector at the 5' end of the scFv. This "tail" should not be biologically active, since its only purpose is the creation of a longer molecule than the native scFv, thus causing a longer retention time in the body.

EXAMPLE 13

FIG. 13 shows the internal cysteine rich repeats in the extracellular domains of the two TNF-Rs and their alignment with the homologous repeats in the extracellular domain of the human FAS, nerve growth factor receptor (NGF) and CDw40, as well as rat Ox40. The amino acid sequences (one letter symbols) are aligned for maximal homology. The positions of the amino acids within the receptors are denoted in the left hand margin.

EXAMPLE 14

Creation of Recombinant DNA Molecules Comprising Nucleotide Sequences Coding for the Active Peptides and Other Molecules and Their Expression The peptides and other molecules can also be prepared by genetic engineering techniques and their preparation encompasses all the tools used in these techniques. Thus DNA molecules are provided which comprise the nucleotide sequence coding for such peptides and other biological molecules. These DNA molecules can be genomic DNA, cDNA, synthetic DNA and a combination thereof.

Creation of DNA molecules coding for such peptides and molecules is carried out by conventional means, once the amino acid sequence of these peptides and other molecules has been determined.

Expression of the recombinant proteins can be effected in eukaryotic cells, bacteria or yeasts, using the appropriate expression vectors. Any method known in the art may be employed.

For example, the DNA molecules coding for the peptides or other molecules obtained by the above methods are inserted into appropriately constructed expression vectors by techniques well known in the art (see Maniatis, T. et al., *Molecular Cloning: Laboratory Manual*, Cold Spring Harbor Laboratory, Cold Spring Harbor (1982)). Double-stranded cDNA is linked to plasmid vectors by homopolymeric tailing or by restriction linking involving the use of synthetic DNA linkers or blunt-ended ligation techniques.

DNA ligases are used to ligate the DNA molecules and undesirable joining is avoided by treatment with alkaline phosphatase.

In order to be capable of expressing a desired biological substance, i.e., a peptide or protein (hereinafter "protein", for simplicity's sake), an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lamda, the bla promoter of the a-lactamase gene of pBR322, and the CAT promoter of the chloramphenicol acetyl transferase gene of pPR325, etc., or inducible, such as the prokaryotic promoters including the major right and left promoters of bacteriophage lambda (Pl and Pr), the trp, recA, lacZ, lacI, ompF and gal promoters of *E. coli*, or the trp-lac hybrid promoter, etc. (Glick, B. R. (1987) *J Ind Microbiol*, :277-282).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno (SD) sequence appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the peptides or other molecules of the invention and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) *Mol Cell Biol*, 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as these capable of replication in *E. coli*, for example, pBR322, ColEl, pSC101, pACYC 184, etc. (see Maniatis et al., (1982) op. cit.); *Bacillus* plasmids such as pC194, pC221, pT127, etc. (Gryczan, T., *The Molecular Biology of the Bacilli*, Academic Press, NY (1982)); Streptomyces plasmids including pIJ101 (Kendall, K. J. et al., (1987) *J Bacteriol* 159:4177-83); *Streptomyces* bacteriophages such as Φ (C31 (Chater, K. F. et al., in: Sixth International Symposium on Actinomycetales Biology, (1986)), and *Pseudomonas* plasmids (John, J. F., et al. (1986) *Rev Infect Dis* 8:693-704; and Izaki, K. (1978) *Jpn J Bacteriol*, 33:729-742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19, pp. 265-274; Broach, J. R., in: The Molecular Biology of the Yeast *Saccharomyces*: Life Cycle and Inheritance, Cold Spring Harbor Laboratory, Cold Spring Harbor, N.Y., pp. 445-470 (1981); Broach, J. R., (1982) *Cell*, 28:203-204; Bollon, D. P., et al. (1980) *J Clin Hematol Oncol*, 10:39-8; Maniatis, T., in: Cell Biology: A Comprehensive Treatise Vol. 3: Gene Expression, Academic Press, NY, pp. 563-608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli, Bacillus, Streptomyces, Pseucomonas, Salmonella, Serratia*, etc. The most preferred prokaryotic host is *E. coli*.

Bacterial hosts of particular interest include *E. coli* K12 strain 294 (ATCC 31446), *E. coli* X1776 (ATCC 31537), *E. coli* W3110 (F⁻, lambda⁻, prototropic (ATCC 27325) ), and other enterobacterium such as *Salmonella typhimurium* or *Serratia marcescens* and various *Pseudomonas* species. Under such conditions, the protein will not be glycosylated. The prokaryotic host must be compatible with the replicon and control sequences in the expression plasmid.

Preferred eukaryotic hosts are mammalian cells, e.g., human, monkey, mouse and Chinese hamster ovary (CHO) cells, because they provide post-translational modifications to prorein molecules including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector, the host cells are grown in a selective medium, which selects for the growth of vector-containing cells. Expression of the cloned gene sequence(s) results in the production of the desired proteins.

Purification of the recombinant proteins is carried out by any one of the methods known for this purpose.

"Increased" or "substantially" increased inhibition of TNF by a ligand or soluble or mutated soluble TNF/NGF receptor means an increase over a suitable control, within experimental error, of at least one selected from the group consisting of 1, 2, 3, 4, 5, 7, 8, 9, 10, 12, 15, 20, 25, 30, 35, 40, 45, 50, 100, 200, 300, 400, 500, or 100,000 percent, or any range or value therein, such as 1000, 2000, 5000, 10,000, 20,000, 50,000, 100, 000%.

What is claimed is:

1. An immunoassay method for the human TNF Binding Protein TBP-II (residues 27-214 of SEQ ID NO:3) in body fluids, comprising:
   obtaining a sample of body fluid from a subject;
   incubating the sample with an antibody to human TBP-II which specifically recognizes and binds said protein; and
   determining the level of human TBP-II in the sample by the level of antibody bound to human TBP-II.

2. A method for the determination of over-production or under-production of TBP-II (residues 27-214 of SEQ ID NO:3) in a subject, using the immunoassay method of claim 1, comprising:
   determining the level of TBP-II in the body fluid of a subject by using said immunoassay; and
   comparing the level so determined with the normal level of TBP-II in human body fluids of healthy subjects, wherein a level above said normal level indicates over-production of TBP-II and a level below said normal level indicates under-production of TBP-II.

* * * * *

SEQUENCE LISTING

```
<160> NUMBER OF SEQ ID NOS: 30

<210> SEQ ID NO 1
<211> LENGTH: 522
<212> TYPE: DNA
<213> ORGANISM: Homo sapiens
<220> FEATURE:
<221> NAME/KEY: CDS
<222> LOCATION: (7)...(516)

<400> SEQUENCE: 1 ctcgag atg aag acc ctg ttc ctg ggt gtc acg ctc ggc ctg gcc gct        48
       Met Lys Thr Leu Phe Leu Gly Val Thr Leu Gly Leu Ala Ala
       1               5                   10 gcc ctg tcc ttc acc ctg gag gag gag gat atc aca ggg acc tgg tac        96
Ala Leu Ser Phe Thr Leu Glu Glu Glu Asp Ile Thr Gly Thr Trp Tyr
 15                  20                  25                  30 gtg aag gcc atg gtg gtc gat aag gac ttt ccg gag gac agg agg ccc       144
Val Lys Ala Met Val Val Asp Lys Asp Phe Pro Glu Asp Arg Arg Pro
                 35                  40                  45
```

| | | |
|---|---|---|
| agg aag gtg tcc cca gtg aag gtg aca gcc ctg ggc ggt ggg aag ttg<br>Arg Lys Val Ser Pro Val Lys Val Thr Ala Leu Gly Gly Gly Lys Leu<br>                    50                        55                      60 | | 192 |
| gaa gcc acg ttc acc ttc atg agg gag gat cgg tgc atc cag aag aaa<br>Glu Ala Thr Phe Thr Phe Met Arg Glu Asp Arg Cys Ile Gln Lys Lys<br>65                        70                        75 | | 240 |
| atc ctg atg cgg aag acg gag gag cct ggc aaa tac agc gcc tat ggg<br>Ile Leu Met Arg Lys Thr Glu Glu Pro Gly Lys Tyr Ser Ala Tyr Gly<br>        80                        85                        90 | | 288 |
| ggc agg aag ctc atg tac ctg cag gag ctg ccc agg agg gac cac tac<br>Gly Arg Lys Leu Met Tyr Leu Gln Glu Leu Pro Arg Arg Asp His Tyr<br>95                        100                    105                    110 | | 336 |
| atc ttt tac tgc aaa gac cag cac cat ggg ggc ctg ctc cac atg gga<br>Ile Phe Tyr Cys Lys Asp Gln His His Gly Gly Leu Leu His Met Gly<br>                    115                    120                    125 | | 384 |
| aag ctt gtg ggt agg aat tct gat acc aac cgg gag gcc ctg gaa gaa<br>Lys Leu Val Gly Arg Asn Ser Asp Thr Asn Arg Glu Ala Leu Glu Glu<br>130                      135                    140 | | 432 |
| ttt aag aaa ttg gtg cag cgc aag gga ctc tcg gag gag gac att ttc<br>Phe Lys Lys Leu Val Gln Arg Lys Gly Leu Ser Glu Glu Asp Ile Phe<br>                    145                    150                    155 | | 480 |
| acg ccc ctg cag acg gga agc tgc gtt ccc gaa cac ggatcc<br>Thr Pro Leu Gln Thr Gly Ser Cys Val Pro Glu His<br>160                    165                    170 | | 522 |

<210> SEQ ID NO 2
<211> LENGTH: 170
<212> TYPE: PRT
<213> ORGANISM: Homo sapiens

<400> SEQUENCE: 2

Met Lys Thr Leu Phe Leu Gly Val Thr Leu Gly Leu Ala Ala Ala Leu
1               5                   10                  15

Ser Phe Thr Leu Glu Glu Glu Asp Ile Thr Gly Thr Trp Tyr Val Lys
            20                  25                  30

Ala Met Val Val Asp Lys Asp Phe Pro Glu Asp Arg Arg Pro Arg Lys
        35                  40                  45

Val Ser Pro Val Lys Val Thr Ala Leu Gly Gly Gly Lys Leu Glu Ala
    50                  55                  60

Thr Phe Thr Phe Met Arg Glu Asp Arg Cys Ile Gln Lys Lys Ile Leu
65                  70                  75                  80

Met Arg Lys Thr Glu Glu Pro Gly Lys Tyr Ser Ala Tyr Gly Gly Arg
                85                  90                  95

Lys Leu Met Tyr Leu Gln Glu Leu Pro Arg Arg Asp His Tyr Ile Phe
            100                 105                 110

Tyr Cys Lys Asp Gln His His Gly Gly Leu Leu His Met Gly Lys Leu
        115                 120                 125

Val Gly Arg Asn Ser Asp Thr Asn Arg Glu Ala Leu Glu Glu Phe Lys
    130                 135                 140

Lys Leu Val Gln Arg Lys Gly Leu Ser Glu Glu Asp Ile Phe Thr Pro
145                 150                 155                 160

Leu Gln Thr Gly Ser Cys Val Pro Glu His
                165                 170

<210> SEQ ID NO 3
<211> LENGTH: 22
<212> TYPE: DNA
<213> ORGANISM: Artificial Sequence
<220> FEATURE:

<223> OTHER INFORMATION: oligonucleotide primer: ZC13139

<400> SEQUENCE: 3
aatggttcgt cctgggcctg gc                                              22

<210> SEQ ID NO 4
<211> LENGTH: 24
<212> TYPE: DNA
<213> ORGANISM: Artificial Sequence
<220> FEATURE:
<223> OTHER INFORMATION: oligonucleotide primer: ZC13937

<400> SEQUENCE: 4
acacctcaaa gcggccatca tcac                                            24

<210> SEQ ID NO 5
<211> LENGTH: 510
<212> TYPE: DNA
<213> ORGANISM: Artificial Sequence
<220> FEATURE:
<223> OTHER INFORMATION: Degenerate sequence derived from human zlipo1
      nucleotide sequence
<220> FEATURE:
<221> NAME/KEY: variation
<222> LOCATION: (1)...(510)
<223> OTHER INFORMATION: n is any nucleotide

<400> SEQUENCE: 5
atgaaracny tnttyytngg ngtnacnytn ggnytngcng cngcnytnws nttyacnytn      60
gargargarg ayathacngg nacntggtay gtnaargcna tggtngtnga yaargaytty    120
ccngargaym gnmgnccnmg naargtnwsn ccngtnaarg tnacngcnyt nggnggnggn    180
aarytngarg cnacnttyac nttyatgmgn gargaymgnt gyathcaraa raarathytn    240
atgmgnaara cngargarcc nggnaartay wsngcntayg gnggnmgnaa rytnatgtay    300
ytncargary tnccnmgnmg ngaycaytay athttytayt gyaargayca rcaycayggn    360
ggnytnytnc ayatgggnaa rytngtnggn mgnaaywsng ayacnaaymg ngargcnytn    420
gargarttya araarytngt ncarmgnaar ggnytnwsng argargayat httyacnccn    480
ytncaracng gnwsntgygt nccngarcay                                     510

<210> SEQ ID NO 6
<211> LENGTH: 8
<212> TYPE: PRT
<213> ORGANISM: Artificial Sequence
<220> FEATURE:
<223> OTHER INFORMATION: Flag affinity peptide

<400> SEQUENCE: 6

Asp Tyr Lys Asp Asp Asp Asp Lys
 1               5

<210> SEQ ID NO 7
<211> LENGTH: 5
<212> TYPE: PRT
<213> ORGANISM: Artificial Sequence
<220> FEATURE:
<223> OTHER INFORMATION: Glu-Glu affinity peptide

<400> SEQUENCE: 7

Glu Tyr Pro Met Glu
 1               5

<210> SEQ ID NO 8

```
-continued

<211> LENGTH: 30
<212> TYPE: DNA
<213> ORGANISM: Artificial Sequence
<220> FEATURE:
<223> OTHER INFORMATION: Oligonucleotide primer: ZC13290

<400> SEQUENCE: 8 gatctagac tagtgttcgg gaacgcagct                                    30

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer: ZC13291

<400> SEQUENCE: 9
cctggatccc tgtccttcac cctggaggag                                   30

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide primer: ZC13270

<400> SEQUENCE: 10
ggactcgaga tgaagaccct gttcctgggt                                   30

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide primer: ZC13271

<400> SEQUENCE: 11
cctggatccg tgttcgggaa cgcagcttcc                                   30

<210> SEQ ID NO 12
<211> LENGTH: 51
<212> TYPE: DNA
<213> ORGANISM: Artificial Sequence
<220> FEATURE:
<223> OTHER INFORMATION: Oligonucleotide primer: ZC13731

<400> SEQUENCE: 12
ggtgtaagct tggacaagag agaagaagaa tacatgccaa tggaaggtgg t            51

<210> SEQ ID NO 13
<211> LENGTH: 63
<212> TYPE: DNA
<213> ORGANISM: Artificial Sequence
<220> FEATURE:
<223> OTHER INFORMATION: Oligonucleotide primer: ZC13762

<400> SEQUENCE: 13
ggtccctgtg atatcctcct cctccagggt gaaggacaga ccaccttcca ttggcatgta   60
ttc                                                                63

<210> SEQ ID NO 14
<211> LENGTH: 44
<212> TYPE: DNA
<213> ORGANISM: Artificial Sequence
<220> FEATURE:
<223> OTHER INFORMATION: Oligonucleotide primer: ZC13497
```

<400> SEQUENCE: 14
agcattgctg ctaaagaaga aggtgtaagc ttggacaaga gaga                            44

<210> SEQ ID NO 15
<211> LENGTH: 52
<212> TYPE: DNA
<213> ORGANISM: Artificial Sequence
<220> FEATURE:
<223> OTHER INFORMATION: Oligonucleotide primer: ZC13764

<400> SEQUENCE: 15
cttatcgacc accatggcct tcacgtacca ggtccctgtg atatcctcct cc                   52

<210> SEQ ID NO 16
<211> LENGTH: 147
<212> TYPE: DNA
<213> ORGANISM: Artificial Sequence
<220> FEATURE:
<223> OTHER INFORMATION: NEE-tagged linker

<400> SEQUENCE: 16
agcattgctg ctaaagaaga aggtgtaagc ttggacaaga gagaagaaga atacatgcca          60
atggaaggtg gtctgtcctt caccctggag gaggaggata tcacagggac ctggtacgtg         120
aaggccatgg tggtcgataa ggacttt                                              147

<210> SEQ ID NO 17
<211> LENGTH: 147
<212> TYPE: DNA
<213> ORGANISM: Artificial Sequence
<220> FEATURE:
<223> OTHER INFORMATION: C-terminal 3' linker

<400> SEQUENCE: 17
cgcaagggac tctcggagga ggacattttc actcccctgc agacgggaag ctgcgttccc          60
gaacactgat agtattctag ggctgcctgt ttggatattt ttataatttt tgagagtttg         120
ccaactaatg ttttctctt ctatgat                                               147

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide primer: ZC13734

<400> SEQUENCE: 18
atcatagaag agaaaaacat tagttggcaa actctcaaaa attataaaaa ta                  52

<210> SEQ ID NO 19
<211> LENGTH: 51
<212> TYPE: DNA
<213> ORGANISM: Artificial Sequence
<220> FEATURE:
<223> OTHER INFORMATION: Oligonucleotide primer: ZC13727

<400> SEQUENCE: 19
cgcaagggac tctcggagga ggacattttc actcccctgc agacgggaag c                   51

<210> SEQ ID NO 20
<211> LENGTH: 63
<212> TYPE: DNA
<213> ORGANISM: Artificial Sequence
<220> FEATURE:

-continued

<223> OTHER INFORMATION: Oligonucleotide primer: ZC13725

<400> SEQUENCE: 20
actcccctgc agacgggaag ctgcgttccc gaacactgat agtattctag ggctgcctgt    60
ttg    63

<210> SEQ ID NO 21
<211> LENGTH: 54
<212> TYPE: DNA
<213> ORGANISM: Artificial Sequence
<220> FEATURE:
<223> OTHER INFORMATION: Oligonucleotide primer: ZC13733

<400> SEQUENCE: 21
tggcaaactc tcaaaaatta taaaaatatc caaacaggca gccctagaat acta    54

<210> SEQ ID NO 22
<211> LENGTH: 51
<212> TYPE: DNA
<213> ORGANISM: Artificial Sequence
<220> FEATURE:
<223> OTHER INFORMATION: Oligonucleotide primer: ZC13735

<400> SEQUENCE: 22
ggtgtaagct tggacaagag agattacaag gacgatgatg acaagggtgg t    51

<210> SEQ ID NO 23
<211> LENGTH: 61
<212> TYPE: DNA
<213> ORGANISM: Artificial Sequence
<220> FEATURE:
<223> OTHER INFORMATION: Oligonucleotide primer: ZC13839

<400> SEQUENCE: 23
ggtccctgtg atatcctcct cctccagggt gaaggacaga ccacccttgt catcatcgtc    60
c    61

<210> SEQ ID NO 24
<211> LENGTH: 147
<212> TYPE: DNA
<213> ORGANISM: Artificial Sequence
<220> FEATURE:
<223> OTHER INFORMATION: N-terminal Flag linker

<400> SEQUENCE: 24
agcattgctg ctaaagaaga aggtgtaagc ttggacaaga gagattacaa ggacgatgat    60
gacaagggtg gtctgtcctt caccctggag gaggagggata tcacagggac ctggtacgtg    120
aaggccatgg tggtcgataa ggacttt    147

<210> SEQ ID NO 25
<211> LENGTH: 6
<212> TYPE: PRT
<213> ORGANISM: Artificial Sequence
<220> FEATURE:
<223> OTHER INFORMATION: Glu-Glu elution peptide

<400> SEQUENCE: 25

Glu Tyr Met Pro Val Asp
 1               5

<210> SEQ ID NO 26
<211> LENGTH: 38
<212> TYPE: DNA

-continued

```
<213> ORGANISM: Artificial Sequence
<220> FEATURE:
<223> OTHER INFORMATION: Oligonucleotide primer: ZC13405

<400> SEQUENCE: 26
cagagagatc tccatgaaga ccctgttcct gggtgtca                              38

<210> SEQ ID NO 27
<211> LENGTH: 31
<212> TYPE: DNA
<213> ORGANISM: Artificial Sequence
<220> FEATURE:
<223> OTHER INFORMATION: Oligonucleotide primer: ZC13406

<400> SEQUENCE: 27 gggggggtacc tagtgttcgg gaacgcagct t                                    31

<210> SEQ ID NO 28
<211> LENGTH: 52
<212> TYPE: DNA
<213> ORGANISM: Artificial Sequence
<220> FEATURE:
<223> OTHER INFORMATION: Oligonucleotide primer: ZC13403

<400> SEQUENCE: 28 gggggggtacc tattccatcg gcatgtattc ttcgtgttcg ggaacgcagc tt             52

<210> SEQ ID NO 29
<211> LENGTH: 176
<212> TYPE: PRT
<213> ORGANISM: Homo sapiens

<400> SEQUENCE: 29
```

Met Lys Pro Leu Leu Leu Ala Val Ser Leu Gly Leu Ile Ala Ala Leu
 1               5                  10                  15

Gln Ala His His Leu Leu Ala Ser Asp Glu Glu Ile Gln Asp Val Ser
            20                  25                  30

Gly Thr Trp Tyr Leu Lys Ala Met Thr Val Asp Arg Glu Phe Pro Glu
        35                  40                  45

Met Asn Leu Glu Ser Val Thr Pro Met Thr Leu Thr Thr Leu Glu Gly
    50                  55                  60

Gly Asn Leu Glu Ala Lys Val Thr Met Leu Ile Ser Gly Arg Cys Gln
65                  70                  75                  80

Glu Val Lys Ala Val Leu Glu Lys Thr Asp Glu Pro Gly Lys Tyr Thr
                85                  90                  95

Ala Asp Gly Gly Lys His Val Ala Tyr Ile Ile Arg Ser His Val Lys
            100                 105                 110

Asp His Tyr Ile Phe Tyr Cys Glu Gly Glu Leu His Gly Lys Pro Val
        115                 120                 125

Arg Gly Val Lys Leu Val Gly Arg Asp Pro Lys Asn Asn Leu Glu Ala
    130                 135                 140

Leu Glu Asp Phe Glu Lys Ala Ala Gly Ala Arg Gly Leu Ser Thr Glu
145                 150                 155                 160

Ser Ile Leu Ile Pro Arg Gln Ser Glu Thr Cys Ser Pro Gly Ser Asp
                165                 170                 175

```
<210> SEQ ID NO 30
<211> LENGTH: 188
<212> TYPE: PRT
<213> ORGANISM: Rattus norvegicus
```

```
<400> SEQUENCE: 30

Met Glu Asn Ile Met Pro Phe Ala Leu Leu Gly Leu Cys Val Gly Leu
 1               5                  10                  15

Ala Ala Gly Thr Glu Gly Ala Val Val Lys Asp Phe Asp Ile Ser Lys
            20                  25                  30

Phe Leu Gly Phe Trp Tyr Glu Ile Ala Phe Ala Ser Lys Met Gly Thr
            35                  40                  45

Pro Gly Leu Ala His Lys Glu Glu Lys Met Gly Ala Met Val Val Glu
        50                  55                  60

Leu Lys Glu Asn Leu Leu Ala Leu Thr Thr Thr Tyr Tyr Ser Glu Asp
 65                 70                  75                  80

His Cys Val Leu Glu Lys Val Thr Ala Thr Glu Gly Asp Gly Pro Ala
                85                  90                  95

Lys Phe Gln Val Thr Arg Leu Ser Gly Lys Lys Glu Val Val Val Glu
                100                 105                 110

Ala Thr Asp Tyr Leu Thr Tyr Ala Ile Ile Asp Ile Thr Ser Leu Val
            115                 120                 125

Ala Gly Ala Val His Arg Thr Met Lys Leu Tyr Ser Arg Ser Leu Asp
        130                 135                 140

Asp Asn Gly Glu Ala Leu Tyr Asn Phe Arg Lys Ile Thr Ser Asp His
145                 150                 155                 160

Gly Phe Ser Glu Thr Asp Leu Tyr Ile Leu Lys His Asp Leu Thr Cys
                165                 170                 175

Val Lys Val Leu Gln Ser Ala Ala Glu Ser Arg Pro
                180                 185
```